(12) United States Patent
Dias et al.

(10) Patent No.: US 11,517,877 B2
(45) Date of Patent: Dec. 6, 2022

(54) SELECTIVE ADSORPTION OF GASEOUS ALKENES INTO NON-POROUS COPPER(I) COMPLEXES: CONTROLLING HEAT OF ADSORPTION AND LOADING PRESSURE

(71) Applicants: Board of Regents, The University of Texas System, Austin, TX (US); University of Canterbury, Christchurch (NZ)

(72) Inventors: Rasika Dias, Arlington, TX (US); Matthew Greig Cowan, Christchurch (NZ); Devaborniny Parasar, Arlington, TX (US)

(73) Assignees: Board of Regents, The University of Texas System, Austin, TX (US); University of Canterbury, Christchurch (NZ)

( * ) Notice: Subject to any disclaimer, the term of this patent is extended or adjusted under 35 U.S.C. 154(b) by 0 days.

(21) Appl. No.: 17/355,743

(22) Filed: Jun. 23, 2021

(65) Prior Publication Data
US 2021/0394155 A1    Dec. 23, 2021

Related U.S. Application Data

(60) Provisional application No. 63/042,884, filed on Jun. 23, 2020.

(51) Int. Cl.
*B01J 20/22* (2006.01)
*C07C 7/12* (2006.01)
*C07F 1/08* (2006.01)
*C07C 7/152* (2006.01)

(52) U.S. Cl.
CPC ............... *B01J 20/223* (2013.01); *C07C 7/12* (2013.01); *C07F 1/08* (2013.01)

(58) Field of Classification Search
CPC ............... B01J 20/223; B01J 20/28033; B01J 20/3204; B01J 20/3208; B01J 20/3236; B01J 20/3242; B01J 20/3433; B01J 20/3483; C07C 7/12; C07C 7/152; C07F 1/08; B01D 69/147
See application file for complete search history.

(56) References Cited

PUBLICATIONS

Jayaratna et al. ("Low Heat of Adsorption of Ethylene Achieved by Major Solid-State Structural Rearrangement of a Discrete Copper(I) Complex." Angew. Chem. Int. Ed. 2018, 57, 16442-16446) (Year: 2018).*

(Continued)

*Primary Examiner* — Youngsul Jeong
*Assistant Examiner* — Jason Y Chong
(74) *Attorney, Agent, or Firm* — Meunier Carlin & Curfman LLC

(57) ABSTRACT

Disclosed are air-stable small-molecule adsorbents trimeric [Cu—Br]$_3$ and [Cu—H]$_3$ that undergo a reversible solid-state molecular rearrangements to [Cu—Br.(alkene)]$_2$ and [Cu—H.(alkene)]$_2$ dimers. The reversible solid-state rearrangement allows one to break adsorbent design trade-offs and achieve low heat of adsorption while retaining high selectivity and uptake.

21 Claims, 10 Drawing Sheets

(56) References Cited

PUBLICATIONS

Parasar et al. ("Synthesis, Photophysical Properties, and Computational Analysis of Di- and Tetranuclear Alkyne Complexes of Copper(I) Supported by a Highly Fluorinated Pyrazolate." Organometallics 2018, 37, 4105-4118) (Year: 2018).*

Parasar et al. ("Carbonyl complexes of copper(I) stabilized by bridging fluorinated pyrazolates and halide ions." Dalton Trans., 2019, 48, 6358-6371) (Year: 2019).*

Allen, John J., and Andrew R. Barron. "Olefin coordination in copper (I) complexes of bis (2-pyridyl) amine." Dalton transactions 5 (2009): 878-890.

Amino, Shuichi, et al. "$C_2H_4$ adsorption on Cu (210), revisited: bonding nature and coverage effects." Physical Chemistry Chemical Physics 18.34 (2016): 23621-23627.

Anson, A., et al. "Adsorption of ethane and ethylene on modified ETS-10." Chemical Engineering Science 63.16 (2008): 4171-4175.

Azhin, Mayam, Tahereh Kaghazchi, and Mohammad Rahmani. "A review on olefin/paraffin separation using reversible chemical complexation technology." Journal of Industrial and Engineering Chemistry 14.5 (2008): 622-638.

Bakhtiari, Omid, and Sepideh Hashemi Safaee. "Industrial grade 1-butene/isobutane separation using supported liquid membranes." Chemical Engineering Research and Design 123 (2017): 180-186.

Bao, Zongbi, et al. "Potential of microporous metal—organic frameworks for separation of hydrocarbon mixtures." Energy & Environmental Science 9.12 (2016): 3612-3641.

Barnett, Brandon R., et al. "Thermodynamic separation of 1-butene from 2-butene in metal—organic frameworks with open metal sites." Journal of the American Chemical Society 141.45 (2019): 18325-18333.

Bloch, Eric D., et al. "Hydrocarbon separations in a metal-organic framework with open iron (II) coordination sites." science 335.6076 (2012): 1606-1610.

Bondarchuk, Sergey V., and Boris F. Minaev. "Thermally accessible triplet state of π-nucleophiles does exist. Evidence from first principles study of ethylene interaction with copper species." RSC Advances 5.15 (2015): 11558-11569.

Bux, Helge, et al. "Ethene/ethane separation by the MOF membrane ZIF-8: molecular correlation of permeation, adsorption, diffusion." Journal of Membrane Science 369.1-2 (2011): 284-289.

Campbell, Christopher, et al. "A transferable model for adsorption in MOFs with unsaturated metal sites." The Journal of Physical Chemistry C 121.1 (2017): 441-458.

Cen, P. L. "Adsorption uptake curves of ethylene on Cu (I)—NaY zeolite." AI Ch. E. Journal (American Institute of Chemical Engineers);(USA) 36.5 (1990).

Changamu, Evans O., Holger B. Friedrich, and Melanie Rademeyer. "Synthesis and structure of the monometallic cationic complex [Cp (CO) 2Fe {η2-(CH2CHCH2CH3)}] PF6 (Cp= η5-C5H5)." Journal of Organometallic Chemistry 693.1 (2008): 164-168.

Chen, Jie, et al. "Adsorptive separation of geometric isomers of 2-butene on gallate-based metal—organic frameworks." ACS applied materials & interfaces 12.8 (2020): 9609-9616.

Chen, Yongwei, et al. "A pillar-layer metal-organic framework for efficient adsorption separation of propylene over propane." Separation and Purification Technology 204 (2018): 75-80.

Chupas, Peter J., et al. "A versatile sample-environment cell for non-ambient X-ray scattering experiments." Journal of Applied Crystallography 41.4 (2008): 822-824.

Cowan, M.G., et al., High Ethene/Ethane Selectivity in 2,2'-Bipyridine-Based Silver(I) Complexes by Removal of Coordinated Solvent. Angewandte Chemie, 2015. 127(19): p. 5832-5835.

Cowan, M.G., et al., High Ethene/Ethane Selectivity in 2,2'-Bipyridine-Based Silver(I) Complexes by Removal of Coordinated Solvent. Angew. Chem., Int. Ed., 2015. 54(19): p. 5740-5743.

Denysenko, Dmytro, et al. "Scorpionate-type coordination in MFU-41 metal—organic frameworks: small-molecule binding and activation upon the thermally activated formation of open metal sites." Angewandte Chemie International Edition 53.23 (2014): 5832-5836.

Dias, HV Rasika, et al. "Brightly phosphorescent trinuclear copper (I) complexes of pyrazolates: Substituent effects on the supramolecular structure and photophysics." Journal of the American Chemical Society 127.20 (2005): 7489-7501.

Dias, HV Rasika, Sharon A. Polach, and Ziyun Wang. "Coinage metal complexes of 3, 5-bis (trifluoromethyl) pyrazolate ligand: Synthesis and characterization of {[3, 5-(CF3) 2Pz] Cu} 3 and {[3, 5-(CF3) 2Pz] Ag} 3." Journal of Fluorine Chemistry 103.2 (2000): 163-169.

Dias, HV Rasika, and Jiang Wu. "Structurally Characterized Coinage-Metal-Ethylene Complexes." European Journal of Inorganic Chemistry 2008.4 (2008): 509-522.

Dias, HV Rasika, and Jiang Wu. "Structurally similar, thermally stable copper (I), silver (I), and gold (I) ethylene complexes supported by a fluorinated scorpionate." Organometallics 31.4 (2012): 1511-1517.

Dolomanov, Oleg V., et al. "OLEX2: a complete structure solution, refinement and analysis program." Journal of applied crystallography 42.2 (2009): 339-341.

Duan, Xing, et al. "A novel NbO-type metal-organic framework for highly separation of methane from C2-hydrocarbon at room temperature." Materials Letters 196 (2017): 112-114.

Durig, J. R., and D. A. C. Compton. "Spectroscopic and thermodynamic study of the conformational properties and torsional potential functions of 1-butene." The Journal of Physical Chemistry 84.7 (1980): 773-781.

EC-BREF, Integrated pollution prevention and control (IPPC) Reference. Institute for Prospective Technological Studies (Technologies for sustainable development) European IPPC Bureau, 2003.

Ehrlich, Stephan, Jonas Moellmann, and Stefan Grimme. "Dispersion-corrected density functional theory for aromatic interactions in complex systems." Accounts of chemical research 46.4 (2013): 916-926.

Eldridge, R. Bruce. "Olefin/paraffin separation technology: a review." Industrial & engineering chemistry research 32.10 (1993): 2208-2212.

Eldrup, Morten, D. Lightbody, and John Neil Sherwood. "The temperature dependence of positron lifetimes in solid pivalic acid." Chemical Physics 63.1-2 (1981): 51-58.

Faas, S., et al. "The ZORA formalism applied to the Dirac-Fock equation." Chemical physics letters 246.6 (1995): 632-640.

Farmanzadeh, Davood, and Tahereh Abdollahi. "A model for the ethylene and acetylene adsorption on the surface of Cun (n= 10-15) nanoclusters: A theoretical study." Applied Surface Science 385 (2016): 241-248.

Ferreira, Alexandre FP, et al. "Suitability of Cu-BTC extrudates for propane—propylene separation by adsorption processes." Chemical engineering journal 167.1 (2011): 1-12.

Fianchini, Mauro, et al. "Use of [SbF6]—to isolate cationic copper and silver adducts with more than one ethylene on the metal center." Organometallics 32.10 (2013): 3034-3041.

Fischer, Michael, et al. "Modeling adsorption in metal—organic frameworks with open metal sites: propane/propylene separations." Langmuir 28.22 (2012): 8537-8549.

Fossdal, A., et al. "Pressure-composition isotherms and thermodynamic properties of TiF3-enhanced Na2LiAlH6." Journal of alloys and compounds 397.1-2 (2005): 135-139.

Froment, G., Thermal cracking for olefins production. Fundamentals and their application to industrial problems. Chemical Engineering Science, 1981. 36(8): p. 1271-1282.

Galassi, Rossana, et al. "Homoleptic cyclic trinuclear d10 complexes: From self-association via metallophilic and excimeric bonding to the breakage thereof via oxidative addition, dative bonding, quadrupolar, and heterometal bonding interactions." Comments on Inorganic Chemistry 39.6 (2019): 287-348.

Gammage, Michael D., et al. "Ethylene binding to Au/Cu alloy nanoparticles." Surface Science 653 (2016): 66-70.

Gao, Fei, et al. "Adsorptive separation of ethylene/ethane mixtures with CuCl@ HY adsorbent: equilibrium and reversibility." Journal of Porous Materials 24.3 (2017): 713-719.

(56) References Cited

PUBLICATIONS

Gao, Fei, et al. "Ethylene/ethane separation by CuCl/AC adsorbent prepared using CuCl2 as a precursor." Adsorption 22.7 (2016): 1013-1022.
Gehre, Mascha, et al. "Sustainable Separations of C4-Hydrocarbons by Using Microporous Materials." ChemSusChem 10.20 (2017): 3947-3963.
Geier, Stephen J., et al. "Selective adsorption of ethylene over ethane and propylene over propane in the metal—organic frameworks M 2 (dobdc)(M= Mg, Mn, Fe, Co, Ni, Zn)." Chemical Science 4.5 (2013): 2054-2061.
Goddard, R., et al. "Structure of 1-butene (trimethylphosphine) zirconocene." Acta Crystallographica Section C: Crystal Structure Communications 46.6 (1990): 998-1001.
Gordon, Christopher P., Richard A. Andersen, and Christophe Copéret. "Metal Olefin Complexes: Revisiting the Dewar—Chatt—Duncanson Model and Deriving Reactivity Patterns from Carbon-13 NMR Chemical Shift." Helvetica Chimica Acta 102.9 (2019): e1900151.
Graham, A. P., et al. "Adsorption, desorption, monolayer structure and dynamics of C 2 H 4 on Cu (001)." Journal of the Chemical Society, Faraday Transactions 92.23 (1996): 4749-4757.
Granato, Miguel A., et al. "Adsorption equilibrium of isobutane and 1-butene in zeolite 13X by molecular simulation." Industrial & engineering chemistry research 47.16 (2008): 6166-6174.
Groom, Colin R., et al. "The Cambridge structural database." Acta Crystallographica Section B: Structural Science, Crystal Engineering and Materials 72.2 (2016): 171-179.
Gucuyener, Canan, et al. "Ethane/ethene separation turned on its head: selective ethane adsorption on the metal—organic framework ZIF-7 through a gate-opening mechanism." Journal of the American Chemical Society 132.50 (2010): 17704-17706.
Gücüyener, Canan, et al. "Facile synthesis of the DD3R zeolite: performance in the adsorptive separation of buta-1, 3-diene and but-2-ene isomers." Journal of Materials Chemistry 21.45 (2011): 18386-18397.
Hahn, Christine, et al. "Coordination of alkenes at a highly electrophilic site. New dicationic platinum (II) complexes: Synthesis, structure, and reactions with nucleophiles." Organometallics 21.9 (2002): 1807-1818.
Hähnel, Thomas, et al. "Adsorptive separation of C2/C3/C4-hydrocarbons on a flexible Cu-MOF: The influence of temperature, chain length and bonding character." Microporous and Mesoporous Materials 224 (2016): 392-399.
Hammersley, A. P., et al. "Two-dimensional detector software: from real detector to idealised image or two-theta scan." International Journal of High Pressure Research 14.4-6 (1996): 235-248.
Hanke, Felix, et al. "Structure and stability of weakly chemisorbed ethene adsorbed on low-index Cu surfaces: performance of density functionals with van der Waals interactions." Journal of Physics: Condensed Matter 24.42 (2012): 424217.
Hayashi, Jun-ichiro, et al. "Separation of ethane/ethylene and propane/propylene systems with a carbonized BPDA—pp 'ODA polyimide membrane." Industrial & engineering chemistry research 35.11 (1996): 4176-4181.
He, Yabing, et al. "Microporous metal—organic frameworks for storage and separation of small hydrocarbons." Chemical Communications 48.97 (2012): 11813-11831.
He, Yabing, Rajamani Krishna, and Banglin Chen. "Metal—organic frameworks with potential for energy-efficient adsorptive separation of light hydrocarbons." Energy & Environmental Science 5.10 (2012): 9107-9120.
Hebben, Nicole, et al. "The electronic structure of the Tris (ethylene) complexes [M (C2H4) 3](M= Ni, Pd, and Pt): A combined experimental and theoretical study." Chemistry—A European Journal 13.36 (2007): 10078-10087.
Herrebout, W. A., and B. J. Van der Veken. "Van der Waals Complexes between Unsaturated Hydrocarbons and Boron Trifluoride: An Infrared and ab Initio Study of Ethene BF3 and Propene BF3." Journal of the American Chemical Society 119.43 (1997): 10446-10454.
Hettiarachchi, Champika V., et al. "Trinuclear Copper (I) and Silver (I) Adducts of 4-Chloro-3, 5-bis (trifluoromethyl) pyrazolate and 4-Bromo-3, 5-bis (trifluoromethyl) pyrazolate." Inorganic chemistry 52.23 (2013): 13576-13583.
Hirsekom, Kurt F., et al. "Thermodynamics, Kinetics, and Mechanism of (silox) 3M (olefin) to (silox) 3M (alkylidene) Rearrangements (silox= tBu3SiO; M= Nb, Ta)." Journal of the American Chemical Society 127.13 (2005): 4809-4830.
Hirsekom, Kurt F., et al. "Olefin Substitution in (silox) 3M (olefin)(silox= t Bu3SiO; M= Nb, Ta): The Role of Density of States in Second vs Third Row Transition Metal Reactivity." Journal of the American Chemical Society 130.4 (2008): 1183-1196.
Ho, WS Winston, et al. "Olefin separations via complexation with cuprous diketonate." Industrial & engineering chemistry research 27.2 (1988): 334-337.
Hopffgarten, Moritz von, and Gernot Frenking. "Energy decomposition analysis." Wiley Interdisciplinary Reviews: Computational Molecular Science 2.1 (2012): 43-62.
Huang, Yun-yang. "Ethylene complexes in copper (I) and silver (I) Y zeolites." Journal of catalysis 61.2 (1980): 461-476.
Iacomi, Paul, et al. "Role of structural defects in the adsorption and separation of C3 hydrocarbons in Zr-fumarate-MOF (MOF-801)." Chemistry of Materials 31.20 (2019): 8413-8423.
Jayaratna, Naleen B., et al. "Isolable arene sandwiched copper (I) pyrazolates." New Journal of Chemistry 39.7 (2015): 5092-5095.
Jayaratna, Naleen B., et al. "Coinage metal pyrazolates [(3, 5-(CF3) 2Pz) M] 3 (M= Au, Ag, Cu) as buckycatchers." Inorganic Chemistry 55.17 (2016): 8277-8280.
Jayaratna, Naleen B., et al. "Low Heat of Adsorption of Ethylene Achieved by Major Solid-State Structural Rearrangement of a Discrete Copper (I) Complex." Angewandte Chemie 130.50 (2018): 16680-16684.
Jin, Mingshi, et al. "Redox-buffer effect of Fe 2+ ions on the selective olefin/paraffin separation and hydrogen tolerance of a Cu+-based mesoporous adsorbent." Journal of Materials Chemistry A 1.22 (2013): 6653-6657.
Kansy, J. "Microcomputer program for analysis of positron annihilation lifetime spectra." Nuclear Instruments and Methods in Physics Research Section A: Accelerators, Spectrometers, Detectors and Associated Equipment 374.2 (1996): 235-244.
Kargol, Marta, et al. "Copper-and Silver-Containing Monolithic Silica-Supported Preparations for Selective Propene—Propane Adsorption from the Gas Phase." Chemistry of materials 17.24 (2005): 6117-6127.
Kazi, Abul B., et al. "Coinage Metal—Ethylene Complexes Supported by Tris (pyrazolyl) borates: A Computational Study." Organometallics 28.6 (2009): 1826-1831.
Khan, Nazmul Abedin, and Sung Hwa Jhung. "Adsorptive removal and separation of chemicals with metal-organic frameworks: contribution of π-complexation." Journal of hazardous materials 325 (2017): 198-213.
Kim, Ah-Reum, et al. "Facile loading of Cu (I) in MIL-100 (Fe) through redox-active Fe (II) sites and remarkable propylene/propane separation performance." Chemical Engineering Journal 331 (2018): 777-784.
Kim, Heejin, Joonho Park, and Yousung Jung. "The binding nature of light hydrocarbons on Fe/MOF-74 for gas separation." Physical Chemistry Chemical Physics 15.45 (2013): 19644-19650.
Kim, Ki Chul, et al. "Computational study of propylene and propane binding in metal—organic frameworks containing highly exposed Cu+ or Ag+ cations." The Journal of Physical Chemistry C 118.17 (2014): 9086-9092.
King, C.J., Separation processes based on reversible chemical complexation. 1987, Wiley: New York, pp. 760-774.
Klimovica, Kristine, Kristin Kirschbaum, and Olafs Daugulis. "Synthesis and properties of "sandwich" diimine-coinage metal ethylene complexes." Organometallics 35.17 (2016): 2938-2943.
Kravchuk, Tatyana, et al. "Ethene adsorption and decomposition on the Cu (410) surface." The Journal of Physical Chemistry C 113.49 (2009): 20881-20889.

(56) References Cited

PUBLICATIONS

Kubota, Jun, et al. "IRAS Studies of adsorbed ethene (C2H4) on clean and oxygen-covered Cu (110) surfaces." The Journal of Physical Chemistry 98.31 (1994): 7653-7656.

Kultaeva, Anastasia, et al. "Selective Gas Adsorption of Alkane/Alkene in a Single-Crystal and Powder Bimetallic Metal—Organic Framework Compound Cu2. 97Zn0. 03 (btc) 2 Studied by Electron Paramagnetic Resonance." The Journal of Physical Chemistry C 123.44 (2019): 26877-26887.

Lamia, Nabil, et al. "Adsorption of propane, propylene and isobutane on a metal—organic framework: Molecular simulation and experiment." Chemical Engineering Science 64.14 (2009): 3246-3259.

Lange, Marcus, et al. "Structural flexibility of a copper-based metal—organic framework: sorption of C 4-hydrocarbons and in situ XRD." Journal of Materials Chemistry A 2.21 (2014): 8075-8085.

Lee, Jae-Wook, et al. "Adsorption Equilibrium and Dynamics of C4 Olefin/Paraffin on π-Complexing Adsorbent." Separation science and technology 39.6 (2005): 1365-1384.

Li, Baiyan, et al. "Introduction of π-complexation into porous aromatic framework for highly selective adsorption of ethylene over ethane." Journal of the American Chemical Society 136.24 (2014): 8654-8660.

Li, Jia, et al. "Metal-organic framework containing planar metal-binding sites: Efficiently and cost-effectively enhancing the kinetic separation of C2H2/C2H4." Journal of the American Chemical Society 141.9 (2019): 3807-3811.

Li, Kunhao, et al. "Zeolitic imidazolate frameworks for kinetic separation of propane and propene." Journal of the American Chemical Society 131.30 (2009): 10368-10369.

Li, Libo, et al. "Ethane/ethylene separation in a metal-organic framework with iron-peroxo sites." Science 362.6413 (2018): 443-446.

Li, Peng, et al. "A microporous six-fold interpenetrated hydrogen-bonded organic framework for highly selective separation of C 2 H 4/C 2 H 6." Chemical communications 50.86 (2014): 13081-13084.

Li, Jian-Rong, Ryan J. Kuppler, and Hong-Cai Zhou. "Selective gas adsorption and separation in metal—organic frameworks." Chemical Society Reviews 38.5 (2009): 1477-1504.

Li, Wu-Wu, Ying Guo, and Wei-Hong Zhang. "A porous Cu (II) metal-organic framework: Synthesis, crystal structure and gas adsorption properties." Journal of Molecular Structure 1143 (2017): 20-22.

Liang, Wanwen, et al. "Ethane selective adsorbent Ni (bdc)(ted) 0.5 with high uptake and its significance in adsorption separation of ethane and ethylene." Chemical Engineering Science 148 (2016): 275-281.

Liang, Wanwen, et al. "Ethane-selective carbon composites CPDA@A-ACs with high uptake and its enhanced ethane/ethylene adsorption selectivity." AIChE Journal 64.9 (2018): 3390-3399.

Liao, Yijun, et al. "Tuning ethylene gas adsorption via metal node modulation: Cu-MOF-74 for a high ethylene deliverable capacity." Chemical Communications 53.67 (2017): 9376-9379.

Lin, Rui-Biao, et al. "Boosting ethane/ethylene separation within isoreticular ultramicroporous metal—organic frameworks." Journal of the American Chemical Society 140.40(2018): 12940-12946.

Linke, R., et al. "Adsorption of ethene on Cu (111)." Surface science 377 (1997): 655-658.

Liu, Kang, et al. "An N-rich metal—organic framework with an rht topology: high CO 2 and C 2 hydrocarbons uptake and selective capture from CH 4." Chemical communications 50.39 (2014): 5031-5033.

Liu, Xiuping, et al. "Anionic NbO-type copper organic framework decorated with carboxylate groups for light hydrocarbons separation under ambient conditions." Journal of materials science 53.12 (2018): 8866-8877.

Luo, Xiaona, et al. "Biased adsorption of ethane over ethylene on low-cost hyper-crosslinked polymers." Journal of Solid State Chemistry 271 (2019): 199-205..

Lv, Daofei, et al. "Selective adsorption of ethane over ethylene in PCN-245: impacts of interpenetrated adsorbent." ACS applied materials & interfaces 10.9 (2018) 8366-8373.

Makino, Takamasa, Michio Okada, and Anton Kokalj. "Adsorption of C2H4 on stepped Cu (410) surface: a combined TPD, FTIR, and DFT study." The Journal of Physical Chemistry C 118.47 (2014): 27436-27448.

Martins, Vanessa FD, et al. "Ethane/ethylene separation on a copper benzene-1, 3, 5-tricarboxylate MOF." Separation and Purification Technology 149 (2015): 445-456.

Martins, Vanessa FD, et al. "High purity ethane/ethylene separation by gas phase simulated moving bed using ZIH-8 adsorbent." AIChE Journal 65.8 (2019): e!6619.

Maslowsky, in Vibrational Spectra of Organometallics (Ed.: E. Maslowsky), John Wiley & Sons, Hoboken, NJ, 2018, pp. 355-370.

McDonald, Thomas M., et al. "Capture of carbon dioxide from air and flue gas in the alkylamine-appended metal—organic framework mmen-Mg2 (dobpdc)." Journal of the American Chemical Society 134.16 (2012): 7056-7065.

McDonald, Thomas M., et al. "Cooperative insertion of CO2 in diamine-appended metal-organic frameworks." Nature 519.7543 (2015): 303-308.

Mehio, Nada, Sheng Dai, and De-en Jiang. "Quantum mechanical basis for kinetic diameters of small gaseous molecules." The Journal of Physical Chemistry A 118.6 (2014): 1150-1154.

Michalak, Artur, Mariusz Mitoraj, and Tom Ziegler. "Bond orbitals from chemical valence theory." The Journal of Physical Chemistry A 112.9 (2008): 1933-1939.

Mofarahi, Masoud, and Seyyed Milad Salehi. "Pure and binary adsorption isotherms of ethylene and ethane on zeolite 5A." Adsorption 19.1 (2013): 101-110.

Moganti, Srinivas, Richard D. Noble, and Carl A. Koval. "Analysis of a membrane/distillation column hydrid process." Journal of membrane science 93.1 (1994): 31-44.

Nijem, Nour, et al. "Tuning the gate opening pressure of metal—organic frameworks (MOFs) for the selective separation of hydrocarbons." Journal of the American Chemical Society 134.37 (2012): 15201-15204.

Oguadinma, Paul O., and Frank Schaper, "π back-bonding in dibenzyl-β-diketiminato copper olefin complexes." Organometallics 28.23 (2009): 6721-6731.

Olivier, Marie-Georges, Karl Berlier, and Roger Jadot. "Adsorption of Butane, 2-Methylpropane, and 1-Butene on Activated Carbon." Journal of Chemical and Engineering Data 39.4 (1994): 770-773.

Omary, Mohammad A., et al. "Metal effect on the supramolecular structure, photophysics, and acid—base character of trinuclear pyrazolato coinage metal complexes." Inorganic chemistry 44.23 (2005): 8200-8210.

Padin, Joel, Ralph T. Yang, and Curtis L. Munson. "New sorbents for olefin/paraffin separations and olefin purification for C4 hydrocarbons." Industrial & engineering chemistry research 38.10 (1999): 3614-3621.

PaláSingh, Anand. "Sorption isotherms of methane, ethane, ethene and carbon dioxide on NaX, NaY and Na-mordenite zeolites." Journal of the Chemical Society, Faraday Transactions 91.17 (1995): 2935-2944.

Pan, Long, et al. "Separation of hydrocarbons with a microporous metal—organic framework." Angewandte Chemie International Edition 45.4 (2006): 616-619.

Parasar, Devaborniny, et al. "Cover Picture: Overcoming Fundamental Limitations in Adsorbent Design: Alkene Adsorption by Non-porous Copper (I) Complexes (Angew. Chem. Int. Ed. 47/2020)." Angewandte Chemie International Edition 59.47 (2020): 20713-20713.https://doi.org/10.1002/anie.202010405.

Parasar, Devaborniny, et al. "Carbonyl complexes of copper (I) stabilized by bridging fluorinated pyrazolates and halide ions." Dalton Transactions 48.19 (2019) 6358-6371.

Parasar, Devaborniny, et al. "Acetylene and terminal alkyne complexes of copper (I) supported by fluorinated pyrazolates: Syntheses, structures, and transformations." Dalton Transactions 48.42 (2019): 15782-15794.

(56) References Cited

PUBLICATIONS

Pedone, Carlo, and Ettore Benedetti. "Absolute configuration and crystal structure of (+)-cis-dichloro [(S)-1-butene][(S)-α-methylbenzylamine] platinum (II)." Journal of Organometallic Chemistry 29.3 (1971): 443-449.

Pires, João, et al. "Enhancement of ethane selectivity in ethane-ethylene mixtures by perfluoro groups in Zr-based metal—organic frameworks." ACS applied materials & interfaces 11.30 (2019): 27410-27421.

Plaza, M. G., et al. "Propane/propylene separation by adsorption using shaped copper trimesate MOF." Microporous and mesoporous materials 157 (2012): 101-111.

Plaza, M. G., et al. "Propylene/propane separation by vacuum swing adsorption using Cu-BTC spheres." Separation and purification technology 90 (2012): 109-119.

Qian, Qihui, et al. "MOF-based membranes for gas separations." Chemical Yeviews 120.16 (2020): 8161-8266. https://doi.org/10.1021/acs.chemrev.0c00119.

Rege, Salil U., Joel Padin, and Ralph T. Yang. "Olefin/paraffin separations by adsorption: π-Complexation vs. kinetic separation." AIChE Journal 44.4 (1998): 799-809.

Rejmak, Pawel, Mariusz Mitoraj, and Ewa Broclawik. "Electronic view on ethene adsorption in Cu (I) exchanged zeolites." Physical Chemistry Chemical Physics 12.10(2010): 2321-2330.

Schaub, Thomas, and Udo Radius. " Efficient C☐F and C☐C Activation by a Novel N-Heterocyclic Carbene-Nickel(0) Comple." Chemistry—A European Journal 11.17 (2005): 5024-5030.

Sheldrick, George M. "A short history of SHELX." Acta Crystallographica Section A: Foundations of Crystallography 64.1 (2008): 112-122.

Shi, Meng, et al. "High pressure adsorptive separation of ethylene and ethane on Na-ETS-10." Chemical engineering science 66.12 (2011): 2817-2822.

Shi, Meng, et al. "Separation of a binary mixture of ethylene and ethane by adsorption on Na-ETS-10." Chemical Engineering Science 65.11 (2010): 3494-3498.

Sholl, David S., and Ryan P. Lively. "Seven chemical separations to change the world." Nature 532.7600 (2016): 435-437.

Siegelman, Rebecca L., et al. "Controlling cooperative CO2 adsorption in diamine-appended Mg2 (dobpdc) metal—organic frameworks." Journal of the American Chemical Society 139.30 (2017): 10526-10538.

Staudt-Bickel, Claudia, and William J. Koros. "Olefin/paraffin gas separations with 6FDA-based polyimide membranes." Journal of Membrane Science 170.2 (2000): 205-214.

Suzuki, Takayuki, Richard D. Noble, and Carl A. Koval. "Electrochemistry, stability, and alkene complexation chemistry of copper (I) triflate in aqueous solution. Potential for use in electrochemically modulated complexation-based separation processes." Inorganic chemistry 36.2 (1997): 136-140.

Takahashi, Akira, et al. "Cu (I)—Y-zeolite as a superior adsorbent for diene/olefin separation." Langmuir 17.26 (2001): 8405-8413.

Tao, S. J. "Positronium annihilation in molecular substances." The Journal of Chemical Physics 56.11 (1972): 5499-5510.

Thakkar, Harshul, et al. "Adsorption of ethane and ethylene over 3d-printed ethane—selective monoliths." ACS Sustainable Chemistry & Engineering 6.11 (2018) 15228-15237.

Toby, Brian H., and Robert B. Von Dreele. "GSAS-II: the genesis of a modem open-source all purpose crystallography software package." Journal of Applied Crystallography 46.2 (2013): 544-549.

Tsou, Dean T., Marc W. Blachman, and James C. Davis. "Silver-facilitated olefin/paraffin separation in a liquid membrane contactor system." Industrial & engineering chemistry research 33.12 (1994): 3209-3216.

Te Velde, G. T., et al. "Chemistry with ADF." Journal of Computational Chemistry 22.9 (2001): 931-967.

Verma, Gaurav, et al. "Partially interpenetrated NbO topology metal—organic framework exhibiting selective gas adsorption." Crystal Growth & Design 17.5 (2017): 2711-2717.

Wagener, Alex, et al. "Metallorganische Koordinationspolymere zur adsorptiven Trennung von Propan/Propen-Gemischen." Chemie Ingenieur Technik 79.6 (2007) 851-855.

Wang, Fei, et al. "Development of a porous coordination polymer with a high gas capacity using a thiophene-based bent tetracarboxylate ligand." ACS applied materials & interfaces 9.39 (2017): 33455-33460.

Wang, Xingjie, et al. "Novel C-PDA adsorbents with high uptake and preferential adsorption of ethane over ethylene." Chemical Engineering Science 155 (2016): 338-347.

Watson, G. W., et al. "π Adsorption of ethene on to the {111} surface of copper: A periodic ab initio study of the effect of k-point sampling on the energy, atomic and electronic structure." Surface science 459.1-2 (2000): 93-103.

Weston, Mitchell H., et al. "High propylene/propane adsorption selectivity in a copper (catecholate)-decorated porous organic polymer." Journal of Materials Chemistry A 2.2 (2014): 299-302.

Wu, Chao, et al. "Comparative study of Ag+-based adsorbents performance in ethylene/ethane separation." Journal of Chemical & Engineering Data 64.2 (2019) 611-618.

Wu, Zhongbiao, et al. "Modification of resin-type adsorbents for ethane/ethylene separation." Industrial & engineering chemistry research 36.7 (1997): 2749-2756.

Xu, Ming-Ming, et al. "Reaction duration-dependent formation of two Cu (ii)-MOFs with selective adsorption properties of C 3 H 4 over C 3 H 6." Dalton Transactions 48.25 (2019): 9225-9233.

Yakovenko, A.A., 2DFLT ver.3.4.3. Upton, Ny, USA: Brookhaven National Laboratory, 2014.

Yan, Jun, et al. "Highly selective adsorption for ethylene, propylene, and carbon dioxide in silver-ionized microporous polyimide." The Journal of Physical Chemistry C 123.1 (2018): 575-583.

Yan, Yong, et al. "Non-interpenetrated metal—organic frameworks based on copper (II) paddlewheel and oligoparaxylene-isophthalate linkers: synthesis, structure, and gas adsorption." Journal of the American Chemical Society 138.10 (2016): 3371-3381.

Yang, Ralph T., and Robert Foldes. "New adsorbents based on principles of chemical complexation: Monolayer-dispersed nickel (II) for acetylene separation by π-complexation." Industrial & engineering chemistry research 35.4 (1996): 1006-1011.

Ye, Zi-Ming, et al. "A new isomeric porous coordination framework showing single-crystal to single-crystal structural transformation and preferential adsorption of 1, 3-butadiene from C4 hydrocarbons." Crystal Growth & Design 17.4 (2017) 2166-2171.

Yoon, Ji Woong, et al. "Controlled reducibility of a metal—organic framework with coordinatively unsaturated sites for preferential gas sorption." Angewandte Chemie International Edition 49.34 (2010): 5949-5952.

Yu, Chao, et al. "A silver (I) coordinated phenanthroline-based polymer with high ethylene/ethane adsorption selectivity." Chemical Communications 50.43 (2014) 5745-5747.

Yu, Lei, et al. "Experimental Study of Silver-Loaded Mesoporous Silica for the Separation of Ethylene and Ethane." Journal of Chemical & Engineering Data 62.9 (2017): 2562-2569.

Zheng, Ji, et al. "Coinage—metal-based cyclic trinuclear complexes with metal—metal interactions: Theories to experiments and structures to functions." Chemical Reviews 120.17 (2020): 9675-9742. https://doi.org/10.1021/acs.chemrev.0c00011.

* cited by examiner

SELECTIVE ADSORPTION OF GASEOUS ALKENES INTO NON-POROUS COPPER(I) COMPLEXES: CONTROLLING HEAT OF ADSORPTION AND LOADING PRESSURE

CROSS REFERENCE TO RELATED APPLICATIONS

This application claims the benefit of priority to U.S. Provisional Application 63/042,884, filed Jun. 23, 2020, which is incorporated by reference herein in its entirety.

STATEMENT ACKNOWLEDGING FINANCIAL SUPPORT

This invention was funded in part by The Welch Foundation under grant number Y-1289.

This invention was made with government support under grant no. CHE 1954456 awarded by the National Science Foundation. The government has certain rights in the invention.

BACKGROUND

Light alkenes such as ethene and propene are produced by cracking hydrocarbon feedstocks such as ethane, propane and naphtha (Froment, G., *Chem. Eng. Sci.,* 1981, 36(8): 1271-1282). The global demand and production of alkenes are higher than any other organic chemical. Annual global production of ethene and propene exceeds 200 million tonnes, and they are used to produce numerous products including polymers and olefin oxides (e.g., ethylene oxide) (Sholl, D. S. et al., *Nature News,* 2016, 532(7600):435).

Industrially, the separation of alkenes from unconverted alkanes is achieved by cryogenic distillation, which requires high pressures and low temperatures due to the similarities in their boiling points and volatility. For example, a distillation column with more than 100 trays operates at temperatures around −25° C. and pressures higher than 2000 kPa (Wu, Z., et al., *Ind. & Eng. Chem. Res.,* 1997, 36(7): 2749-2756). This energy-intensive separation process contributes to almost 75% of the total alkene production cost (Anson, A., et al., *Chem. Eng. Sci.,* 2008, 63(16):4171-4175) and accounts for about 0.3% of global energy use. Several methods have been investigated to reduce the energy consumption and the cost of these separation processes. These include membrane (Hayashi, J.-I., et al., *Ind. & Eng. Chem. Res.,* 1996, 35(11):4176-4181; Staudt-Bickel, C., et al., *J. Membr. Sci.,* 2000, 170(2):205-214; Azhin, M., et al., *J. Ind. Eng. Chem.,* 2008, 14(5):622-638; Bux, H., et al., J. Membrane Sci., 2011, 369(1-2):284-289; Tsou, D. T., et al., *Ind. & Eng. Chem. Res.,* 1994, 33(12):3209-3216), adsorption (Gücüyener, C., et al., *J. Am. Chem. Soc.,* 2010, 132(50): 17704-17706; Gücüyener, C., et al., *J. Mater. Chem.,* 2011, 21(45):18386-18397; Shi, M., et al., *Chem. Eng. Sci.,* 2010, 65(11):3494-3498; Shi, M., et al., *Chem. Eng. Sci.,* 2011, 66(12):2817-2822), or hybrid separation methods that combine distillation with membrane processes (Moganti, S., et al., *J. Membr. Sci.,* 1994, 93(1):31-44).

Complexing agents such as silver and copper have been explored to improve adsorption and membrane separation processes (King, C. J., Separation processes based on reversible chemical complexation. 1987, Wiley: New York. p. 760-774). These metals reversibly interact with then-electrons of alkenes (Khan, N. A., et al., *J. Hazardous Mater.,* 2017, 325:198-213; Dias, H. V. R., et al., *Eur. J. Inorg. Chem.,* 2008, 509-522; Yang, R. T., et al., *Ind. & Eng. Chem. Res.,* 1996, 35(4):1006-1011). The π-electrons provide a distinguishing feature to separate alkenes from alkanes, enhancing the selectivity and capacity of materials, leading to process designs with higher product purity, recovery, and through-put.

What are thus needed are new materials and methods for adsorption of alkenes. The compositions and methods disclosed herein addresses these and other needs.

SUMMARY

In accordance with the purposes of the disclosed devices, systems and methods as embodied and broadly described herein, the disclosed subject matter related to devices and systems, methods of making said devices and systems, and methods of using said devices and systems. More specifically, disclosed herein is a composition comprising an alkene and a compound having Formula I:

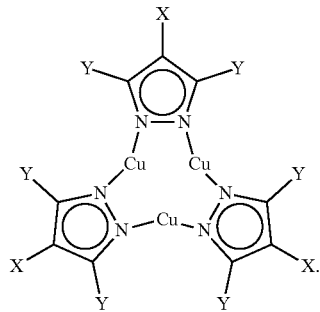

I

Also, disclosed are compositions comprising complexes having Formula II

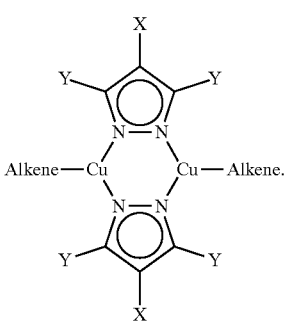

II

In Formula I and II, each X is, independent of the other, chosen from H, $CH_3$, $CF_3$, $C_2F_5$, $C_3F_7$, $C_4F_8$, F, Cl, Br and I; and each Y is, independent of the other, chosen from $CF_3$, $C_2F_5$, $C_3F_7$, $C_4F_8$, F, Cl, Br, and I. In the disclosed compositions, the alkene (Alkene) can be ethene, propene, 1-butene, or 2-butene, or mixtures thereof. In other examples, an alkane such as ethane, propane, or butane or mixtures thereof can be present. The alkene can be part of a gas or liquid stream. Methods of separating an alkene from a mixture of the alkene and an alkane are also disclosed, the method comprising contacting the compound having Formula I with the mixture and forming the complex having Formula II. The alkene can then be recovered from the complex having Formula II by reducing the pressure or by raising the temperature or by using both pressure and temperature variations. Articles comprising the compounds having Formula I and/or complexes having Formula II and a substrate are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying drawings, which are incorporated and constitute a part of this specification, illustrate several aspects of the disclosure, and together with the description, serve to explain the principles of the disclosure.

FIG. 4, bottom, is a top view of the powder diffraction patterns for the $[Cu—H.(C_2H_4)]_2$ ethylene desorption experiment. Black and grey arrows show calculated major peak positions for $[Cu—H]_3$ and $[Cu—H.(C_2H_4)]_2$, respectively.

DETAILED DESCRIPTION

Solid adsorbents are of interest due to the potential efficiency of solid/gas operations such as temperature and pressure swing adsorption (Bao, Z., et al., *Energy & Environ. Sci.*, 2016, 9(12):3612-3641). Adsorbent design currently requires trade-offs between desirable properties. Increasing capacity via surface area decreases selectivity; increasing selectivity via strengthening interactions also increases heat of adsorption and affects isotherm shape; and using absorption instead of adsorption decreases kinetics. The cost of these trade-offs is manifested in process design. For example, decreasing overall heat of adsorption is economically preferable because it means less cooling or heating energy is required to maintain the adsorbent temperature during operation.

Adsorbents with 'step'-shaped isotherms, where the majority of gas uptake occurs over a narrow pressure range, could be applied to pressure or temperature swing processes requiring relatively small amounts of energy (McDonald, T. M., et al., *Nature*, 2015, 519(7543):303-308). Ideally, isotherm 'steps' would occur above atmospheric pressure at moderate temperatures (ca. 100 kPa, 25° C.) to avoid the capital and operational expense of vacuum swing adsorption. However, there are few known mechanisms for achieving 'step'-shaped isotherms, limited to 'gate-opening' (Nijem, N., et al., *J. Am. Chem. Soc.*, 2012, 134(37):15201-15204) and cooperative adsorption of carbon dioxide in metal organic frameworks (McDonald, T. M., et al., *J. Am. Chem. Soc.*, 2012, 134(16):7056-7065; Siegelman, R. L., et al., *J. Am. Chem. Soc.*, 2017, 139(30):10526-10538), small-molecule adsorbents (Cowan, M. G., et al., *Angew. Chem.*, 2015, 127(19):5832-5835; Jayaratna, N. B., et al., *Angew. Chem.*, 2018, 130(50):16680-16684), and hydride salts (Fossdal, A., et al., *J. Alloys Comp.*, 2005, 397(1-2):135-139). Through the Claussius-Clapeyron relationship, positioning the 'step' pressure above 100 kPa at moderate temperature requires larger heat of adsorption, an undesirable trade-off due to the extra operational energy required from large heats of adsorption. Another trade-off is that step-shaped isotherms also produce non-sharpening wave-fronts in breakthrough configurations, requiring alternate separation process designs to maximize adsorbent productivity.

Figure 1:
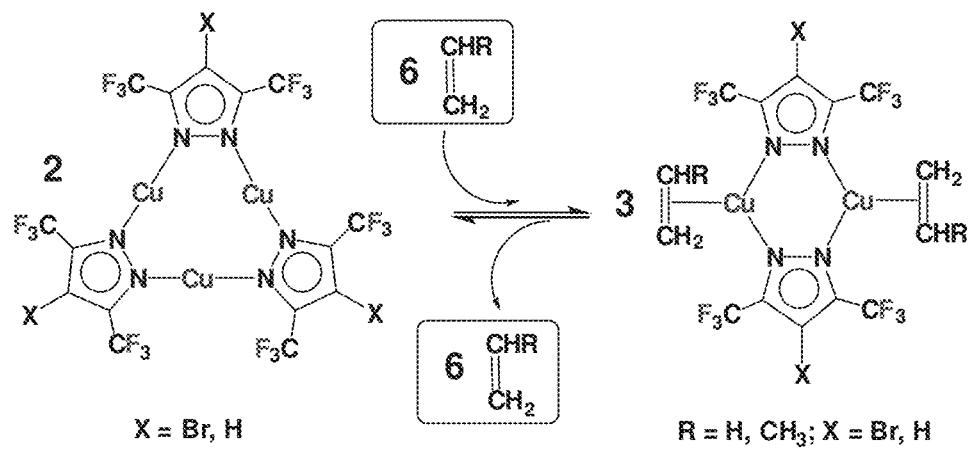
FIG. 1 shows the structures of trinuclear $\{[4\text{-Br-3,5-}(CF_3)_2Pz]Cu\}_3$ ($[Cu—Br]_3$) and $\{[3,5\text{-}(CF_3)_2Pz]Cu\}_3$ ($[Cu—H]_3$) and their chemistry with ethene and propene leading to dinuclear $[Cu—Br.(C_2H_4)]_2$, $[Cu—H.(C_2H_4)]_2$, $[Cu—Br.(C_3H_6)]_2$, and $[Cu—H.(C_3H_6)]_2$.

In the present disclosure, traditional trade-offs for adsorbent design are avoided using an olefin-responsive, solid-state structural rearrangement mechanism. The air-stable and cheap trimeric complexes $\{[4\text{-Br-}3,5\text{-}(CF_3)_2Pz]Cu\}_3$ ([Cu—Br]$_3$) (Hettiarachchi, C. V., et al., *Inorg. Chem.*, 2013, 52(23):13576-13583) and $\{[3,5\text{-}(CF_3)_2Pz]Cu\}_3$ ([Cu—H]$_3$) (Dias, H. V. R., et al., *J. Fluorine Chem.*, 2000, 103(2):163-169) (FIG. 1) rearrange to the dimeric species [Cu—Br.$(C_2H_4)]_2$ and [Cu—H.$(C_2H_4)]_2$, respectively. As alkene adsorbent materials, they feature high capacity, high selectivity, fast rates of adsorption and desorption, and low heat of adsorption for the gaseous alkenes ethene and propene compared to other alkene adsorbents. Furthermore, [Cu—H]$_3$ undergoes alkene adsorption above 100 kPa at 20° C. and rapid desorption when exposed to atmosphere, allowing operation above atmospheric pressure and avoiding the requirement for vacuum swing adsorption process designs.

Compositions

In specific examples disclosed herein is a compound having Formula I:

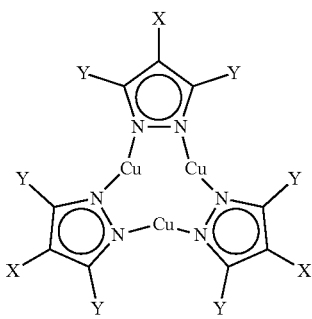

I wherein each X is, independent of the other, chosen from H, $CH_3$, $CF_3$, $C_2F_5$, $C_3F_7$, $C_4F_8$, F, Cl, Br and I; and each Y is, independent of the other, chosen from $CF_3$, $C_2F_5$, $C_3F_7$, $C_4F_8$, F, Cl, Br, and I. In specific examples, X can be chosen from H, Br, $CF_3$, and $CH_3$, e.g., H or Br.

In other specific examples, Y can be $CF_3$.

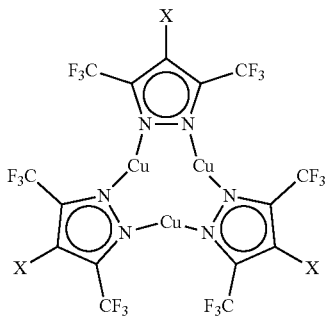

wherein each X is, independent of the other, chosen from H, $CH_3$, $CF_3$, $C_2F_5$, $C_3F_7$, $C_4F_8$, F, Cl, Br and I.

In further examples, disclosed herein are compositions comprising an alkene and the compound having Formula I. The alkene can be ethene, propene, 1-butene, 2-butene or mixtures thereof. Further the composition can comprise an alkane. The alkanes can be ethane, propane, butane or mixtures thereof.

In still further examples, disclosed herein is a complex having Formula II:

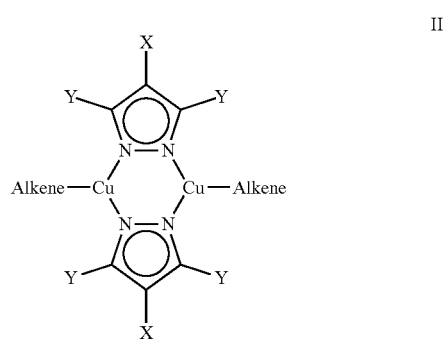

II wherein each X is, independent of the other, chosen from H, $CH_3$, $CF_3$, $C_2F_5$, $C_3F_7$, $C_4F_8$, F, Cl, Br and I; and each Y is, independent of the other, chosen from $CF_3$, $C_2F_5$, $C_3F_7$, $C_4F_8$, F, Cl, Br, and I. In further examples, X can be chosen from H, Br, $CF_3$, and $CH_3$, e.g., H or Br.

In other specific examples, Y can be $CF_3$.

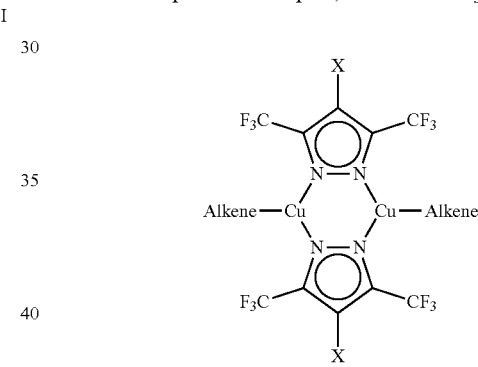

wherein each X is, independent of the other, chosen from H, $CH_3$, $CF_3$, $C_2F_5$, $C_3F_7$, $C_4F_8$, F, Cl, Br and I.

In still other examples, Alkene can be ethene, propene, 1-butene, 2-butene, or mixtures thereof. Without wishing to be bound by theory, the complexes of Formula II can be present with compounds of Formula I and an alkene, and such compositions are expressly contemplated and disclosed herein.

It should be noted that while Formula II shows a solid line between a copper atom and "Alkene", this is not meant to imply a single (σ) bond. It is meant merely to illustrate a coordination of the copper to the alkene.

In still further examples, disclosed herein are adsorption materials comprising the composition of Formula I and/or Formula II and a substrate. The substrate can be a bead, film, particle, or membrane, which can be made of either an inorganic or polymeric substrate. In some examples, the adsorption materials can be in a fixed and/or fluidized bed, e.g., in a fixed and/or fluidized bed temperature and/or pressure swing adsorption process.

Methods

Disclosed herein are methods of separating an alkene from a mixture comprising the alkene and an alkane, comprising contacting the mixture with the compound having Formula I to form a complex having Formula II, wherein the Alkene moiety in the complex is the alkene being separated from the mixture. In some examples, the mixture can be contacted with the compound having Formula I at a pressure below a partial pressure of the Alkene, e.g., the alkene's partial pressure is above the pressure of the contacting step in the isotherm at the operating temperature. In specific examples, contacting the compound having Formula I with the mixture can occur at pressures at or above ambient pressure.

The alkene can be ethene, propene, 1-butene, 2-butene, or a mixture thereof. The alkane can be ethane, propane, butane or mixtures thereof. In some embodiments the alkane can be separated from other gas mixtures. While not wishing to be bound by theory, the alkene can be separated from any gas that does not contain a carbon-carbon double bond and/or pi electrons that would interact with the compounds having Formula I. For example, alkenes can be separated from $N_2$, methane, carbon dioxide.

The mixture can be contacted with the composition having Formula I at any temperature up to the decomposition temperature of the compounds having Formula I, which can be up to approximately 200° C. In some specific examples, the mixture can be contacted with the composition having Formula I at from 0° C. to 200° C., from 0° C. to 150° C., from 0° C. to 100° C., from 0° C. to 65° C., from 0° C. to 50° C., from 0° C. to 40° C., from 0° C. to 30° C., from 0° C. to 20° C., from 0° C. to 10° C., from 10° C. to 40° C., from 10° C. to 30° C., from 10° C. to 20° C., from 20° C. to 40° C., from 20° C. to 30° C., or from 30° C. to 40° C. In further examples, the mixture can be contacted with the composition having Formula I at 0, 10, 20, 30, 40, 50, 60, 70, 80, 90, 100, 110, 120, 130, 140, 150, 160, 170, 180, 190, or 200° C., where any of the stated values can form an upper or lower endpoint of a range.

In still other examples, the mixture can be contacted with the composition of Formula I at pressures from ambient pressure to 100 kPa. In still other examples, the mixture can be contacted with the composition of Formula I at pressures from 100 kPa to 100,000 kPa, e.g., from 600 kPa to 1000 kPa. In specific examples the pressure can be 100 kPa, 200 kPa, 300 kPa, 400 kPa, 500 kPa, 600 kPa, 700 kPa, 800 kPa, 900 kPa, 1000 kPa, 2000 kPa, 5000 kPa, 10,000 kPa, 50,000 kPa, or 100,000 kPa, where any of the stated values can form an upper or lower endpoint of a range.

In other examples, the pressure can be reduced to ambient pressure or below after forming the complex having Formula II and the alkene can be isolated or recovered. In other examples, the temperature can be increased after forming the complex having Formula II and the alkene, can be isolated or recovered. Still further, the pressure and temperature can be adjusted to conditions that result in the release of the alkene from the complex having Formula II and the alkene can then be isolated or recovered.

In still further examples, the method can be a solid-state method wherein the compound having Formula I is in its solid state when contacted with the alkene. Yet in other examples, the compound having Formula I can be contacted with the alkene in the presence of a solvent. Examples of suitable solvents include methylene chloride and chloroform.

Examples

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. Efforts have been made to ensure accuracy with respect to numbers (e.g., amounts, temperatures, etc.); however, some errors and deviations should be accounted for. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

All manipulations were carried out under an atmosphere of purified nitrogen using standard Schlenk techniques unless otherwise noted. Solvents were purchased from commercial sources and distilled prior to use. NMR spectra were recorded at 25° C. on a JEOL Eclipse 500 ($^1$H, 500.16 MHz; $^{13}$C, 125.78 MHz; $^{19}$F, 470.62 MHz), unless otherwise noted. Proton and carbon chemical shifts are reported in ppm versus $Me_4Si$. $^{19}$F NMR values were referenced to external $CFCl_3$. Melting points were obtained on a Mel-Temp II apparatus and were not corrected. Raman data were collected on a Horiba Jobin Yvon LabRAM Aramin Raman spectrometer with a HeNe laser source of 633 nm. The $\{[4\text{-Br-}3,5\text{-}(CF_3)_2Pz]Cu\}_3$ ([Cu—Br]$_3$) (Hettiarachchi, C. V., et al., Trinuclear Copper (I) and Silver (I) Adducts of 4-Chloro-3,5-bis(trifluoromethyl) pyrazolate and 4-Bromo-3,5-bis (trifluoromethyl) pyrazolate. Inorg. Chem. 2013, 52(23):13576-13583) and $\{[3,5\text{-}(CF_3)_2Pz]Cu\}_3$ ([Cu—H]$_3$) (Dias, H. V. R., et al., Coinage metal complexes of 3,5-bis (trifluoromethyl) pyrazolate ligand: Synthesis and characterization of $\{[3,5\text{-}(CF_3)_2Pz]Cu\}_3$ and $\{[3,5\text{-}(CF_3)_2Pz]Ag\}_3$. J. Fluorine Chem. 2000, 103(2):163-169) were prepared according to reported literature procedures with a slight modification. Gas sorption measurements were performed using a volumetric adsorption machine (Quantachrome-Autosorb-iQ2). In situ high-gas pressure diffraction data of [Cu—H]$_3$ in ethene atmosphere were collected using the monochromatic X-rays available at the 17-BM (0.45238 Å) beamline (300 μm diameter beam size) at the Advanced Photon Source, Argonne National Laboratory in combination with a VAREX 4343 amorphous-Si flat panel detector. Thermogravimetric analysis (TGA) was performed on an Alphatech SDT Q600 TGA/DSC under an inert nitrogen atmosphere. Samples were heated from 20° C. to 800° C. at a rate of 10° C.·min$^{-1}$. All other reactants and reagents were purchased from commercial sources.

Synthesis of [(4-Br-3,5-(CF$_3$)$_2$Pz)Cu(H$_2$C=CH$_2$)]$_2$, referred as ([Cu—Br.(C$_2$H$_4$)]$_2$)

$\{[4\text{-Br-}3,5\text{-}(CF_3)_2Pz]Cu\}_3$ ([Cu—Br]$_3$) (0.3 g, 0.289 mmol) was dissolved in ~10 mL of dichloromethane, and a gentle stream of ethene was bubbled into the solution for ~8-10 min. The solution was kept at −20° C. to obtain X-ray quality colorless crystals of [Cu—Br.(C$_2$H$_4$)]$_2$. Yield: 95%. M.p.: 210-215° C. (melted with a temperature similar to that observed for [Cu—Br]$_3$ indicating the clean loss of ethene). Raman (neat, cm$^{-1}$): 3097, 3081, 3062, 2992, 1909, 1542, 1517, 1443, 1361, 1281, 1188, 1179, 1158, 1140, 1035, 968, 960, 815, 746. Room temperature NMR data: $^1$H NMR (in CDCl$_3$): δ (ppm) 4.64 (br s, 2H, CH$_2$). $^{19}$F NMR (in CDCl$_3$): δ (ppm) −60.07 (s). $^{13}$C$\{^1$H$\}$ NMR (in CDCl$_3$): δ (ppm) 85.4 (br s, CH$_2$=CH$_2$), 91.3 (s, C-4), 120.6 (q, $^1J_{C\text{-}F}$=270.3 Hz, CF$_3$), 141.2 (q, $^2J_{C\text{-}F}$=35.6 Hz, C-3/C-5). [Cu—Br]$_3$ and free ethene generated due to ethene dissociation from [Cu—Br.

$(C_2H_4)]_2$ are also present in the mixture. Low temperature (−60° C.) NMR data. $^1$H NMR (in CDCl$_3$): δ (ppm) 4.45 (br s, 2H, CH$_2$). $^{19}$F NMR (in CDCl$_3$): δ (ppm) −59.67 (s). $^{13}$C{$^1$H} NMR (in CDCl$_3$): δ (ppm) 84.0 (br s, CH$_2$=CH$_2$), 91.1 (s, C-4), 120.2 (q, $^1J_{C\text{-}F}$=262.7 Hz, CF$_3$), 140.5 (q, $^2J_{C\text{-}F}$=37.6 Hz, C-3/C-5). The presence of traces of [Cu—Br]$_3$ generated as a result of ethene dissociation from [Cu—Br.(C$_2$H$_4$)]$_2$ was observed as very minor signals in the mixture.

Synthesis of [(4-Br-3,5-(CF$_3$)$_2$Pz)Cu (H$_2$C=CHCH$_3$)]$_2$ ([Cu—Br.(C$_3$H$_6$)]$_2$)

A dichloromethane solution of ([Cu—Br]$_3$) (0.25 g, 0.241 mmol) was concentrated by bubbling a gentle stream of propene gas through the solution and kept at −20° C. to obtain X-ray quality colorless crystals of [Cu—Br.(C$_3$H$_6$)]$_2$. Yield: 86%. M.p.:195° C. (melted at a temperature similar to that observed for [Cu—Br]$_3$). Raman (neat, cm$^{-1}$): 3080, 3002, 2977, 2928, 1546, 1517, 1447, 1356, 1264, 1164, 935, 894. Room temperature NMR data with excess propene: $^1$H NMR (in CDCl$_3$): δ (ppm) 1.70 (br s, 3H, CH$_3$), 4.55 (br s, 2H, CH$_2$), 5.53 (br s, 1H, CH). $^{19}$F NMR (in CDCl$_3$): δ (ppm) −60.29 (s). $^{13}$C{$^1$H} NMR (in CDCl$_3$): δ (ppm) 19.7 (s, CH$_3$), 83.4 (br s, =CH$_2$), =CHCH$_3$ peak could not be observed, 91.0 (s, C-4), 120.7 (q, $^1J_{C\text{-}F}$=271.1 Hz, CF$_3$), 141.0 (q, $^2J_{C\text{-}F}$=38.4 Hz, C-3/C-5). Signals for free propene (present in excess) and [Cu—Br]$_3$ generated due to dissociation of propene from [Cu—Br.(C$_3$H$_6$)]$_2$ were also observed. Low temperature (−40° C.) NMR data with excess propene: $^1$H NMR (in CDCl$_3$): δ (ppm) 1.62 (br s, 3H, CH$_3$), 4.20 (br s, 0.5H, CH$_2$), 4.26 (br s, 0.5H, CH$_2$), 4.37 (br s, 1H, CH$_2$), 5.25 (br s, 1H, CH). $^{19}$F NMR (in CDCl$_3$): δ (ppm) −59.84 to −60.20 (several singlets). $^{13}$C{$^1$H} NMR (in CDCl$_3$): δ (ppm) 19.8 (s, CH$_3$), 82.6 (br s, =CH$_2$), 83.1 (br s, =CH$_2$), 90.8 (s, C-4), 100.7 (br s, =CHCH$_3$), 101.3 (br s, =CHCH$_3$), 120.4 (q, $^1J_{C\text{-}F}$=268.7 Hz, CF$_3$), 140.5 (q, $^2J_{C\text{-}F}$=36.4 Hz, C-3/C-5). No signs for the presence of [Cu—Br]$_3$ in the NMR spectra. Peaks for free propene (present in excess) were observed.

Synthesis of [(3,5-(CF$_3$)$_2$Pz)Cu(H$_2$C=CH$_2$)]$_2$ ([Cu—H.(C$_2$H$_4$)]$_2$)

{[3,5-(CF$_3$)$_2$Pz]Cu}$_3$ ([Cu—H]$_3$) (0.35 g, 0.437 mmol) was dissolved in ~12 mL of dichloromethane and stirred for ~10-12 min under a slow stream of ethene. The reaction mixture was concentrated with a continuous flow of ethene and kept at −20° C. to obtain X-ray quality colorless crystals of [3,5-(CF$_3$)$_2$Pz)Cu(H$_2$C=CH$_2$)]$_2$, ([Cu—H.(C$_2$H$_4$)]$_2$). Yield: 92%. M.p.: 180-185° C. (melted at a temperature similar to that observed for [Cu—H]$_3$ indicating the clean loss of ethene). Raman (neat, cm$^{-1}$), selected peaks: 2986, 1537, 1511, 1450, 1370, 1270, 1157, 1136, 997. Room temperature NMR data: $^1$H NMR (in CDCl$_3$): δ (ppm) 6.84 (s, 2H, Pz-H), ethene signal appears as a broad peak at 5.08 ppm. $^{19}$F NMR (in CDCl$_3$): δ (ppm) −59.96 (s). $^{13}$C{$^1$H} NMR (in CDCl$_3$): δ (ppm) 104.1 (s, C-4), 121.1 (q, $^1J_{C\text{-}F}$=268.7 Hz, CF$_3$), 142.5 (q, $^2J_{C\text{-}F}$=36.8 Hz, C-3/C-5). [Cu—H]$_3$ and free ethene generated due to ethene dissociation from [Cu—H.(C$_2$H$_4$)]$_2$ are also present in the mixture. Low temperature (−60° C.) NMR data: $^1$H NMR (in CDCl$_3$): δ (ppm) 6.85 (s, 2H, Pz-H), 4.48 (br s, 8H, bound CH$_2$=CH$_2$). $^{19}$F NMR (in CDCl$_3$): δ (ppm) −59.48 (s). $^{13}$C{$^1$H} NMR (in CDCl$_3$): δ (ppm) 83.2 (s, bound CH$_2$=CH$_2$), 104.2 (s, C-4), 120.8 (q, $^1J_{C\text{-}F}$=268.3 Hz, CF$_3$), 141.9 (q, $^2J_{C\text{-}F}$=37.2 Hz, C-3/C-5). Very minor amounts of free ethene and [Cu-11]3 generated due to ethene dissociation from [Cu—H.(C$_2$H$_4$)]$_2$ are also present in the mixture.

Synthesis of [(3,5-(CF$_3$)$_2$Pz)Cu(H$_2$C=CHCH$_3$)]$_2$ ([Cu—H.(C$_3$H$_6$)]$_2$)

{[3,5-(CF$_3$)$_2$Pz]Cu}$_3$ ([Cu—H]$_3$) (0.25 g, 0.312 mmol) was dissolved in ~8 mL of dichloromethane and stirred for ~8-10 min while bubbling propene as a gentle stream into the solution. The reaction mixture was concentrated with a continuous flow of propene and kept at −20° C. to obtain X-ray quality colorless crystals of [Cu—H.(C$_3$H$_6$)]$_2$. Yield: 91%. M.p.: 185° C. (melted at a temperature similar to that observed for [Cu—H]$_3$ indicating the clean loss of propene). Raman (neat, cm$^{-1}$): 3157, 2960, 2901, 1538, 1504, 1456, 1403, 1358, 1255, 1182, 1160, 1138, 988, 923, 888, 850, 800. Room temperature NMR data with excess propene: $^1$H NMR (in CDCl$_3$): δ (ppm) 1.72 (br d, 6H, CH$_3$), 4.93 (br s, 2H, CH$_2$), 5.02 (br d, 2H, CH$_2$), 5.82 (br s, 2H, CH), 6.82 (s, 2H, Pz-H). $^{19}$F NMR (in CDCl$_3$): δ (ppm) −60.29 (s). $^{13}$C{$^1$H} NMR (in CDCl$_3$): δ (ppm) 103.6 (br, C-4), no other peaks for [Cu—H.(C$_3$H$_6$)]$_2$ were observed. Peaks for free propene (present in excess) and [Cu—H]$_3$ generated as a result of dissociation of propene from [Cu—H.(C$_3$H$_6$)]$_2$ were also observed. Low temperature (−60° C.) NMR data with excess propene: $^1$H NMR (in CDCl$_3$): δ (ppm) 1.59 (br m, 6H, CH$_3$), 4.19 (br d, 1H, CH$_2$), 4.29 (br d, 1H, CH$_2$), 4.36 (br s, 2H, CH$_2$), 5.25 (br s, 2H, CH), 6.82 (br s, 2H, Pz-H). $^{19}$F NMR (in CDCl$_3$): δ (ppm) −59.74 to −60.06 (several singlets presumably due to isomers resulting of cis/trans propene orientation). $^{13}$C{$^1$H} NMR (in CDCl$_3$): δ (ppm) 19.9 (s, CH$_3$), 81.7 (br s, =CH$_2$), 82.0 (br s, =CH$_2$), 99.0 (br s, =CHCH$_3$), 99.5 (br s, =CHCH$_3$), 103.6 (s, C-4), 120.6 (q, $^1J_{C\text{-}F}$=220.7 Hz, CF$_3$), 141.4 (br q, C-3/C-5). Peaks for free propene (present in excess) were also observed.

Characterization

Trinuclear copper(I) complexes [Cu—Br]$_3$ and [Cu—H]$_3$ adsorb ethene and propene in a reversible manner both in solution and in solid state (FIG. 1). [Cu—Br]$_3$ and [Cu—H]$_3$ in CH$_2$C$_{12}$ solutions react with ethene to produce [Cu—Br.(C$_2$H$_4$)]$_2$ and [Cu—H.(C$_2$H$_4$)]$_2$, respectively, which were isolated under an ethene atmosphere as colourless crystalline solids at −20 C. Bulk purity was established using Raman spectroscopy to verify the presence of metal bound alkenes.

Figure 2:
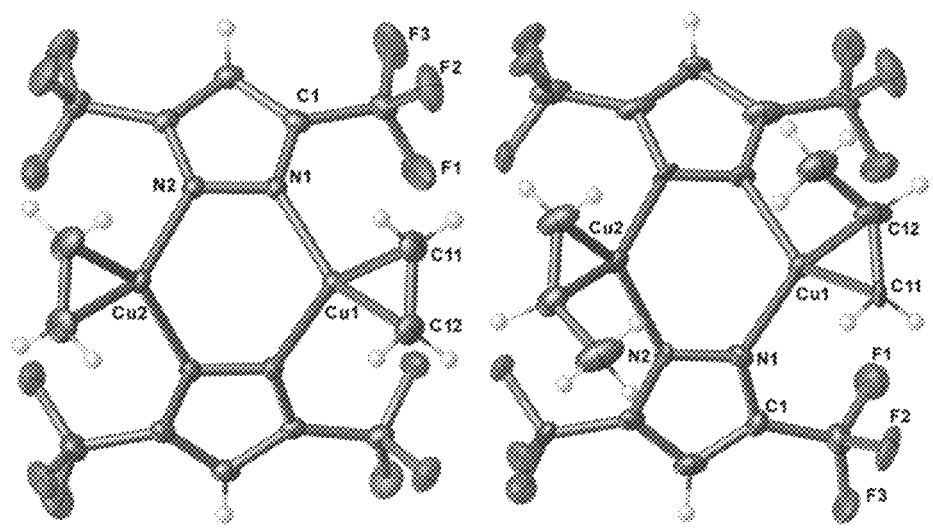
FIG. 2 shows molecular structures of $[Cu—H.(C_2H_4)]_2$ (left) and $[Cu—H.(C_3H_6)]_2$ (right, illustrating only the trans-propene conformation). The $[Cu—Br.(C_2H_4)]_2$ and $[Cu—Br.(C_3H_6)]_2$ analogs also have dinuclear structures.

The X-ray crystal structures at 100 K of the ethene complexes [Cu—Br.(C$_2$H$_4$)]$_2$ and [Cu—H.(C$_2$H$_4$)]$_2$ show that they are dinuclear species, in contrast to the trinuclear [Cu—Br]$_3$ and [Cu—H]$_3$. The dimers adopt boat-shaped Cu$_2$N$_4$ cores (FIG. 2). The analogous copper(I) propene complexes [Cu—Br.(C$_3$H$_6$)]$_2$ and [Cu—H.(C$_3$H$_6$)]$_2$, were synthesized via a similar route and are also dinuclear structures and form crystals with two propene moieties adopting cis and trans-conformation in the solid state (FIG. 2), which is consistent with low temperature NMR spectroscopic data of these samples. From searches in the Cambridge Structural Database, [Cu—Br.(C$_3$H$_6$)]$_2$ and [Cu—H.(C$_3$H$_6$)]$_2$ appear to be the first examples of structurally characterized copper(I)-propene complexes. The occurrence of this remarkable gas-induced trimer to dimer conversion in the solid-state, involving the breaking and formation of several bonds, is the origin of the very attractive gas adsorption properties described below.

In CDCl$_3$ solution, trinuclear precursors and dinuclear products are in fast equilibrium (FIG. 1) on the NMR time scale and can be driven toward the copper-alkene products upon lowering the temperature. Van't Hoff analysis of the $^1$H, $^{19}$F and $^{13}$C VT-NMR data provided the enthalpy change for this alkene uptake in solution as −22 and −35 kJ·mol$^{-1}$ per Cu-ethene interaction for the formation of [Cu—Br.(C$_2$H$_4$)]$_2$ and [Cu—H.(C$_2$H$_4$)]$_2$, respectively. The corresponding propene adduct formations are slightly more exothermic at −34 and −39 kJ·mol$^{-1}$ per Cu-propene interaction, respectively. In general, propene has higher heat of adsorption than ethene, and the observation here is probably a reflection of favourable interactions between the more electron rich propene with the Lewis acidic Cu(I) sites (although many other factors can complicate such a simple explanation considering the large structural reorganization during alkene coordination process).

Solid samples of these copper-alkene complexes lose alkene at room temperature upon removal from alkene atmosphere, with the ethene adducts showing greater propensity for the alkene loss under similar conditions.

Figure 3:
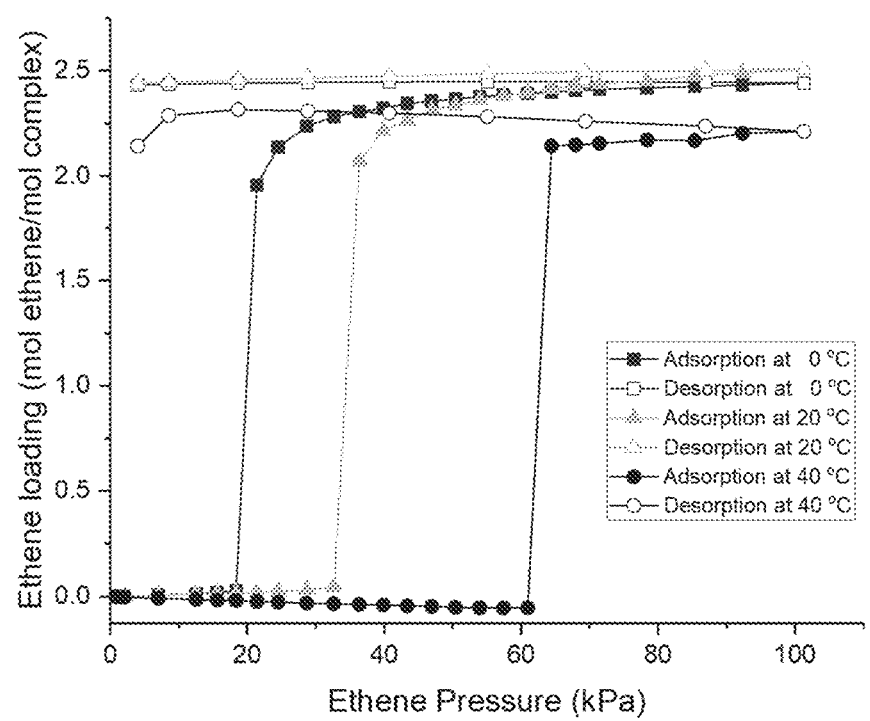
FIG. 3 is a graph showing ethene adsorption (solid symbols) and desorption (hollow symbols) isotherms of $[Cu—Br]_3$ at 0, 20, and 40° C.

Single-gas adsorption isotherms were measured up to 100 kPa and 20° C. to quantify the pressure-dependent ethene uptake by [Cu—Br]$_3$ and [Cu—H]$_3$ in the solid-state. While [Cu—Br]$_3$ showed an ethene uptake of 2.51 mol$_{ethene}$·mol$_{complex}^{-1}$, [Cu—H]$_3$ showed almost zero uptake below 100 kPa. The step-shaped isotherm (similar to IUPAC Type V) for [Cu—Br]$_3$ showed that ≤80% loading capacity can be obtained in one 'step' by increasing pressure from 30 to 35 kPa (FIG. 3).

The negligible ethene uptake of [Cu—H]$_3$ at 100 kPa and 20° C. suggested that the 'step' in ethene uptake had been shifted to pressures above 101 kPa. Exposing [Cu—H]$_3$ to higher pressures (636-682 kPa) using a house-built apparatus resulted in ethene loadings of ≤2.5 mol$_{ethene}$·mol$_{complex}^{-1}$.

Equilibrium adsorption isotherms were collected for [Cu—Br]$_3$ at 0, 20 and 40° C. (FIG. 3) to examine the effect of temperature on the step pressure and determine the heat of adsorption as −20.7 kJ·mol$^{-1}{}_{Cu3}$; −10.0 kJ·mol$^{-1}{}_{Cu.C2H4}$ interaction. For comparison, the heat of adsorption of ethene for the heavily fluorinated [Cu—CF$_3$]$_3$ was −38 kJ·mol$^{-1}{}_{Cu3}$; −13.1 kJ·mol$^{-1}{}_{Cu.C2H4}$ interaction (Jayaratna, N. B., et al., *Angew. Chem.*, 2018, 130(50):16680-16684). The Clausius-Clapeyron relation predicts that the 'step' pressures of ethene adsorption at given temperature should increase with increasing heat of adsorption. However, the step pressures vary in the order [Cu—CF$_3$]$_3$<[Cu—Br]$_3$<[Cu—H]$_3$; contrary to prediction. This can be explained by considering that the observed heat of adsorption is the combination of the exothermic heat of adsorption from ethene binding and the endothermic trimer to dimer phase change induced by ethene coordination. These results demonstrate that the design strategy of increasing the energy of ethene binding while counter-balancing with increasing the phase change energy breaks trade-offs in adsorbent design and can be used to position the ethene uptake 'step' pressure independent of overall heat of adsorption.

Figure 4:
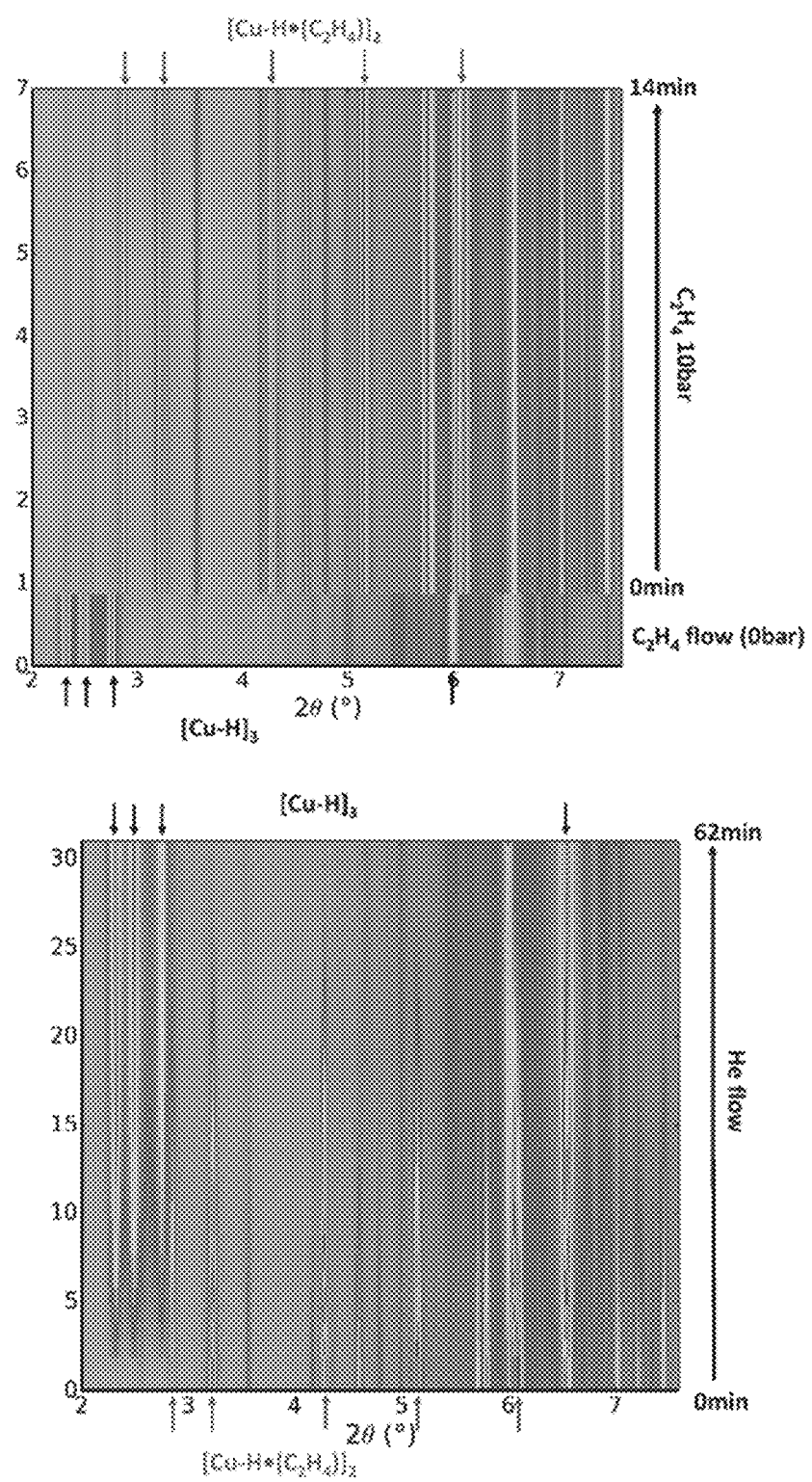
FIG. 4, top, is a top view of the powder diffraction patterns for the $[Cu—H]_3$ ethene loading experiment. Black and grey arrows show calculated major peak positions for $[Cu—H]_3$ and $[Cu—H.(C_2H_4)]_2$, respectively.

To definitively attribute the mechanism of ethene uptake to rapid conversions between trimeric [Cu—H]$_3$ and [Cu—Br]$_3$ and their corresponding dimeric ethene complexes, in-situ PXRD measurements were performed at 17-BM beamline at the Advanced Photon Source, Argonne National Laboratory (FIG. 4). Specifically, in situ high-gas pressure diffraction data from [Cu—H]$_3$ and [Cu—Br]$_3$ in ethene atmosphere were collected using the monochromatic X-rays available at the 17-BM. Beams (300 μm diameter beam size) with 0.45238 Å wavelength were used for [Cu—H]$_3$ samples and 0.24117 Å wavelength was used for [Cu—Br]$_3$ experiments at the Advanced Photon Source, Argonne National Laboratory in combination with a VAREX 4343 amorphous-Si flat panel detector. Samples of [Cu—H]$_3$ and [Cu—Br]$_3$ were loaded into 1.0 mm quartz capillaries with glass wool on either side. The capillary with sample was then loaded into the gas flow-cell, to perform in situ PXRD experiments. At one end the gas cell was connected to a two-way valve which allowed changing between a 1 atm helium flow and a high-pressure syringe pump (Teledyne ISCO 500D) which was filled with ethene gas.

Figure 5:
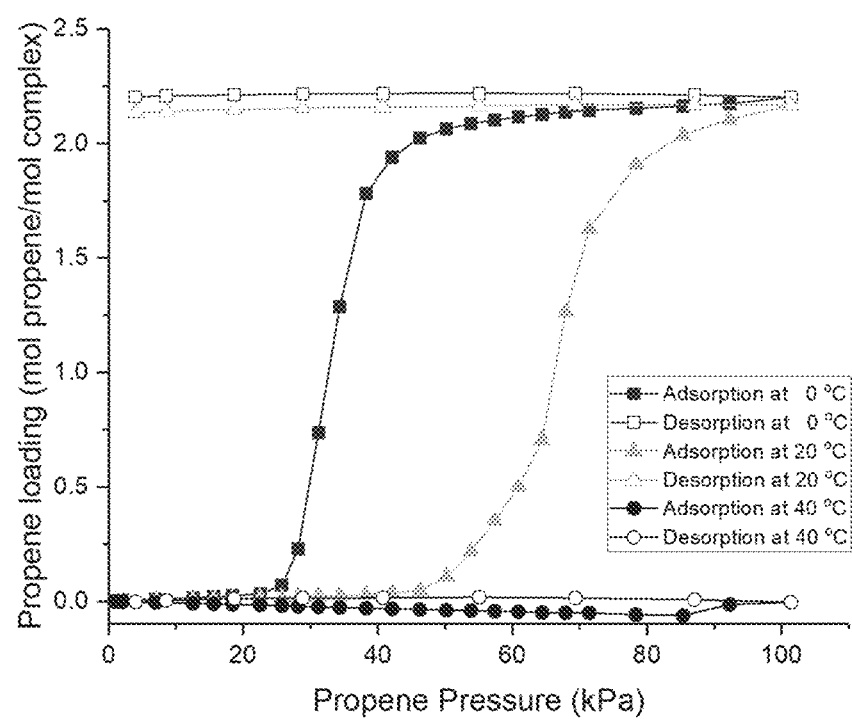
FIG. 5 is a graph showing propene adsorption (solid symbols) and desorption (hollow symbols) isotherms of $[Cu—Br]_3$ at 0, 20 and 40° C.

A remarkable solid-state to solid-state transformation of trinuclear copper precursors to dimeric [Cu—H.(C$_2$H$_4$)]$_2$ and [Cu—Br.(C$_2$H$_4$)]$_2$ was observed under a high pressure ethene atmosphere (FIG. 5). The existence of all structures was confirmed by correlation to the simulated PXRD data generated from single-crystal structures.

Under ethene flow at 100 kPa, there is little formation of [Cu—H.(C$_2$H$_4$)]$_2$ after 10 min. When the pressure of ethene was raised to 10 bar (1000 kPa) >95% [Cu—H]$_3$ instantly transformed into [Cu—H.(C$_2$H$_4$)]$_2$ (FIG. 4, top). The entire conversion process completed in under 15 min. The resulting product is stable under an ethene atmosphere, however [Cu—H.(C$_2$H$_4$)]$_2$ converts back to [Cu—H]$_3$ when placed in a flow of helium. Complete conversion to [Cu—H]$_3$ is achieved within an hour, with the majority of conversion occurring within the first 15 minutes (FIG. 4, bottom).

Incredibly, the remarkable trimer to dimer solid-state observed for ethene could be extended to the larger alkene propene. The propene equilibrium adsorption isotherms for [Cu—Br]$_3$ and [Cu—H]$_3$ at 20° C. showed uptakes of 2.17 and ca. 0 mol$_{propene}$·mol$_{complex}^{-1}$ of [Cu—Br]$_3$ and [Cu—H]$_3$, respectively (FIG. 5). 90% of propene loading could be obtained by swinging the pressure between 45 and 75 kPa. This confirmed that even the larger alkene was able to penetrate the dense crystalline material and induce the reversible trimer to dimer structural rearrangement in the solid state.

As with ethene, increasing the temperature increased the 'step' pressure. However, no uptake was observed at 40° C., indicating that the step pressure at 40° C. is likely above 100 kPa. [Cu—H]$_3$ therefore has potential for use in a temperature swing adsorption process around 100 kPa where minor temperature changes of ca. 20° C. could lead to the adsorption/release of most of the alkene gas.

[Cu—H]$_3$ was tested for propene uptake at ca. 519 kPa and showed loading of 2.2 mol$_{propene}$·mol$_{complex}^{-1}$. As with ethene, this exceptional behaviour raises potential for [Cu—H]$_3$ to be used in temperature swing adsorption processes operating above 100 kPa.

High alkene:alkane selectivities were observed because alkanes cannot coordinate to the copper(I) centres. Both [Cu—Br]$_3$ and [Cu—H]$_3$ showed low uptake of the alkanes ethane and propane (<0.1 mol$_{gas}$·mol$_{complex}^{-1}$), as expected for solids with low surface area. Ideal ethene/ethane and propene/propane selectivities for [Cu—Br]$_3$ were calculated from the equilibrium loadings at 101 kPa and 20° C. as 47:1 and 40:1, respectively. The ethene/ethane selectivity of [Cu—H]$_3$ at 620 kPa was 47:1 and propene/propane selectivity at 440 kPa was 29:1. This selectivity is higher than most of the adsorbents reported in the literature.

In the past, investigations into small-molecule absorbents have suggested that the small surface areas will limit the gas adsorption and desorption rates. The surface areas of [Cu—Br]$_3$ and [Cu—H]$_3$ are less than 16 m$^2$·g$^{-1}$ and uptake rates at 100 kPa are slow. Notably, the ethene and propene adsorption rates are fast (90% loading and >75% loading within 3 minutes) when [Cu—Br]$_3$ and [Cu—H]$_3$ are loaded at high pressure (>600 kPa and >440 kPa, respectively). Repeated cycles clearly demonstrate the reproducibility of these rapid adsorption and desorption rates.

Figure 6:
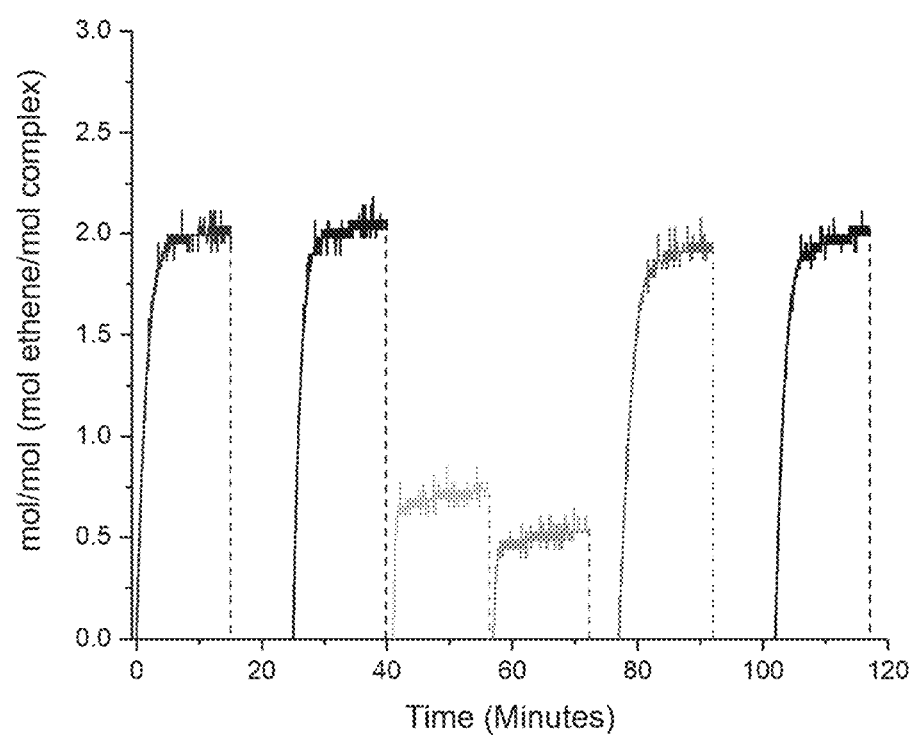
FIG. 6 is a graph showing ethene adsorption/desorption cycles for the $[Cu—H]_3/[Cu—H.(C_2H_4)]_2$ complex. The $[Cu—H]_3$ was treated with ethene at 600 kPa for 15 minutes between desorption cycles. The resulting $[Cu—H.(C_2H_4)]_2$ complex was then exposed to at 100 kPa regular atmosphere for various times 1, 5 and 10 minutes. 1st: after initial vacuum desorption; $2^{nd}$ and $6^{th}$ peaks: after 10 min atmosphere exposure; $3^{rd}$ and $4^{th}$ peaks: after 1 min; $5^{th}$ peak: after 5 min.

Cycling a sample of [Cu—H]$_3$ between an ethene pressure of ca. 600 kPa and atmospheric pressure (i.e., opening the adsorption cell and exposing the sample to atmosphere) revealed that 90% of the adsorption capacity was regenerated within ≤10 minutes (FIG. 6). Likewise, propene is desorbed within <15 minutes when exposed to atmosphere. This relatively rapid rate of desorption is in contrast to the small-molecule adsorbents reported previously, which required extended periods under vacuum and elevated temperature to induce ethene desorption.

To probe the transport of ethene within these materials, Positron Annihilation Spectroscopy (PALS) was used to investigate changes in free-volume between the trimer and dimer configurations. The average free volume element sizes within [Cu—Br]$_3$ and [Cu—H]$_3$ were 0.581, and 0.301 nm; compared to the kinetic diameter of ethene (0.4163 nm) (He, Y., et al., *Chem. Commun.* 2012. 48(97):11813-11831). However, these internal free volumes did not correlate to the adsorption kinetics, with [Cu—H]$_3$ being faster. [Cu—H]$_3$ has the shortest lifetime, and hence smallest free volume element size, however it featured the highest intensity, therefore showing considerable free volume. The smaller free volume element size, 0.3 nm, is too small for the adsorption of ethene through the solid, potentially explaining why increased pressure is needed for the ethene to convert the structure.

The trimeric copper complexes [Cu—Br]$_3$ and [Cu—H]$_3$ undergo a remarkable solid-state transformation to dimeric species upon exposure to the gaseous alkenes ethene and propene, mimicking solution chemistry. This allows one to break trade-offs in adsorbent design between heat of adsorption and selectivity, isotherm 'step' pressure, and capacity. For [Cu—H]$_3$, adsorption is rapid at high pressures, and the reversibility was observed to occur within minutes indirectly (e.g., regeneration of adsorption capacity) after exposure to atmosphere, and directly via reduction of ethene partial pressure using helium gas (in-situ PXRD). Alkene capacity approaches 1 mol/mol loadings per copper site, and the low surface area of [Cu—Br]$_3$ and [Cu—H]$_3$ combined with the selectivity of the adsorption mechanism lead to high alkene/alkane 'adsorption' selectivities of >47 for ethene:ethane and >29 for propene:propane. Finally, the structural arrangement concurrent with the alkene adsorption results in low overall heat of adsorption 10-20 kJ mol$^{-1}_{ethene}$. In summary, the material [Cu—H]$_3$ embodies an ideal alkene/alkane adsorbent, breaking traditional trade-offs to achieve high capacity, selectivity, fast adsorption and desorption kinetics, low heat of adsorption, stability in ambient air, and process operation above atmospheric pressure.

Synthesis of {[3,5-(CF$_3$)$_2$Pz]Cu(H$_2$C=CHC$_2$H$_5$)}$_2$ ([Cu—H.(C$_4$H$_8$)]$_2$)

{[3,5-(CF$_3$)$_2$Pz]Cu}$_3$ ([Cu—H]$_3$) (0.4 g, 0.5 mmol) was dissolved in ~10 mL of dichloromethane. The solution was concentrated with 1-butene and kept at −20° C. to obtain X-ray quality colorless crystals of [Cu—H.(C$_4$H$_8$)]$_2$. Yield: 86%. M.p.: 175-180° C. (melted at a temperature similar to that observed for [Cu—H]$_3$ indicating the clean loss of 1-butene). Raman (neat, cm$^{-1}$): 3161, 2973, 2933, 2903, 2870, 1534, 1504, 1443, 1245, 1135, 987, 931. Elemental data of the vacuum dried materials indicate the loss of butene and the formation of [Cu—H]$_3$. Room temperature NMR data: $^1$H NMR (in CDCl$_3$): δ (ppm) 1.00 (t, J=7.3 Hz, 6H, CH$_3$), 2.06 (br s, 4H, CH$_2$), 4.28 (br s, 2H, CH$_2$), 4.42 (br s, 2H, CH$_2$), 5.39 (br s, 2H, CH), 6.81 (s, 2H, Pz-H). $^{19}$F NMR (CDCl$_3$): δ (ppm) −60.11 (s). $^{13}$C{$^1$H} NMR (CDCl$_3$): δ (ppm) 13.3 (s, CH$_3$), 26.9 (s, CH$_2$), 103.8 (s, C-4), 122.3 (CF$_3$), 142.2 (q, $^2$J$_{C-F}$=25.2 Hz, C-3/C-5). Peaks for [Cu—H]$_3$ and free 1-butene, that are in dynamic equilibrium with [Cu—H.(C$_4$H$_8$)]$_2$ were also observed. Room temperature NMR data with excess 1-butene: $^1$H NMR (in CDCl$_3$): δ (ppm) 1.01 (t, J=7.3 Hz, 6H, CH$_3$), 2.06 (br s, 4H, CH$_2$), 4.92 (br s, 2H, CH$_2$), 5.00 (br s, 2H, CH$_2$), 5.87 (br s, 2H, CH), 6.82 (s, 2H, Pz-H). $^{19}$F NMR (CDCl$_3$): δ (ppm) −60.10 (s). $^{13}$C{$^1$H} NMR (CDCl$_3$): δ (ppm) 13.3 (s, CH$_3$), 26.9 (s, CH$_2$), 103.8 (s, C-4), 121.2 (q, $^1$J$_{C-F}$=268.7 Hz, CF$_3$), 142.2 (q, $^2$J$_{C-F}$=37.6 Hz, C-3/C-5). Peaks for [Cu—H]$_3$ resulting from 1-butene dissociation and excess 1-butene were observed. These species are in dynamic equilibrium with [Cu—H.(C$_4$H$_8$)]$_2$. Low temperature (−40° C.) NMR data with excess 1-butene: $^1$H NMR (in CDCl$_3$): δ (ppm) 0.98 (t, J=7.4 Hz, 6H, CH$_3$), 1.93 (br s, 4H, CH$_2$), 4.18 (br d, 1H, CH$_2$) 4.27 (br d, 1H, CH$_2$), 4.37 (br d, 2H, CH$_2$), 5.32 (br s, 2H, CH), 6.82 (s, 2H, Pz-H). $^{19}$F NMR (CDCl$_3$): δ (ppm) −59.61 to −59.97 (several fine singlets). $^{13}$C{$^1$H} NMR (CDCl$_3$): δ (ppm) 13.9 (s, CH$_3$), 14.4 (s, CH$_3$), 26.8 (s, CH$_2$), 79.4 (s, =CH$_2$), 80.0 (s, =CH$_2$), 103.7 (s, C-4), 106.3 (br s, =CHC$_2$H$_5$), 106.6 (br s, =CHC$_2$H$_5$), 120.9 (q, CF$_3$), 141.7 (q, $^2$J$_{C-F}$=36.0 Hz, C-3/C-5). No [Cu—H]$_3$ signals were observed at −40° C. Peaks for excess 1-butene were also observed.

Synthesis of {[4-Br-3,5-(CF$_3$)$_2$Pz]Cu(H$_2$C=CHC$_2$H$_5$)}2 ([Cu—Br.(C$_4$H$_8$)]$_2$)

{[4-Br-3,5-(CF$_3$)$_2$Pz]Cu}$_3$ ([Cu—Br]$_3$) (0.4 g, 0.386 mmol) was dissolved in ~10-12 mL of dichloromethane and stirred for about 8-10 min while bubbling 1-butene. The reaction mixture was concentrated with a continuous flow of 1-butene and kept at −20° C. to obtain X-ray quality colorless crystals of [Cu—Br.(C$_4$H$_8$)]$_2$. Yield: 93%. M.p.: 180-185° C. (melted at a temperature similar to that observed for [Cu—Br]$_3$ indicating the clean loss of 1-butene). Raman (neat, cm$^{-1}$): 3074, 3013, 2982, 2936, 2903, 2878, 2846, 1535, 1506, 1434, 1341, 1272, 1250, 1166, 1133, 1023, 1007, 961, 930, 837, 821. Elemental data of the vacuum dried materials indicate the loss of butene and the formation of [Cu—Br]$_3$. Room temperature NMR data: $^1$H NMR (in CDCl$_3$): δ (ppm) 1.00 (t, J=7.3 Hz, 6H, CH$_3$), 2.02 (br s, 4H, CH$_2$), 4.28 (br s, 1H, CH$_2$), 4.47 (br s, 1H, CH$_2$), 5.37 (br s, 1H, CH). $^{19}$F NMR (CDCl$_3$): δ (ppm) −60.06 (s). $^{13}$C{$^1$H} NMR (CDCl$_3$): δ (ppm) 13.5 (s, CH$_3$), 27.1 (s, CH$_2$), 81.3 (br s, =CH$_2$, no=CHC$_2$H$_5$ peak was observed), 91.0 (s, C-4), 120.7 (q, $^1$J$_{C-F}$=270.3 Hz, CF$_3$), 140.9 (q, $^2$J$_{C-F}$=35.6 Hz, C-3/C-5). Free 1-butene and [Cu—Br]$_3$ generated as a result of dissociation of 1-butene from [Cu—Br.(C$_4$H$_8$)] also present in the mixture and their signal were also observed. All these species are in a dynamic equilibrium. Low temperature (−60° C.) NMR data: $^1$H NMR (in CDCl$_3$): δ (ppm) 0.97 (t, J=7.3 Hz, 3H, CH$_3$), 1.91 (br d, 2H, CH$_2$), 4.15 (d, 0.5H, CH$_2$), 4.25 (d, 0.5H, CH$_2$), 4.34 (d, 1H, CH$_2$), 5.28 (br d, 1H, CH). $^{19}$F NMR (CDCl$_3$): δ (ppm) −59.54 to −59.87 (several fine singlets). $^{13}$C{$^1$H} NMR (CDCl$_3$): δ (ppm) 14.2 (s, CH$_3$), 14.6 (s, CH$_3$), 27.0 (s, CH$_2$), 27.2 (s, CH$_2$), 80.2 (s, =CH$_2$), 80.9 (s, =CH$_2$), 90.8 (s, C-4), 107.7 (s, =CHC$_2$H$_5$), 107.9 (s, =CHC$_2$H$_5$), 120.3 (q, $^1$J$_{C-F}$=268.3 Hz, CF$_3$), 140.2 (br q, C-3/C-5). Very minor peaks for free 1-butene and [Cu—Br]$_3$ were observed in $^1$H and $^{19}$F NMR, however no such peaks were observed in $^{13}$C{$^1$H} NMR.

Characterization

[Cu—H]$_3$ and [Cu—Br]$_3$ react with 1-butene in solvents like dichloromethane to yield [Cu—H.(C$_4$H$_8$)]$_2$ and [Cu—

Figure 7:
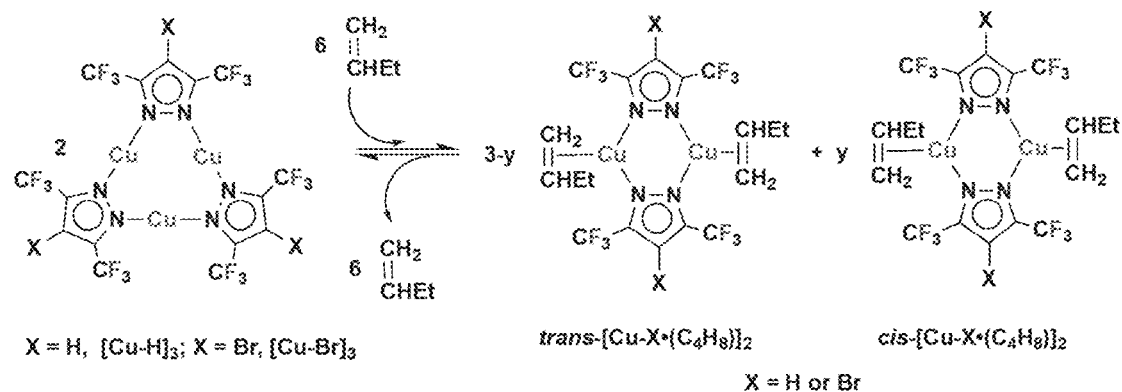
FIG. 7 shows the syntheses of dinuclear 1-butene complexes, $\{[3,5\text{-}(CF_3)_2Pz]Cu(H_2C=CHC_2H_5)\}_2$ ($[Cu—H.(C_4H_8)]_2$) and $\{[4\text{-Br-3,5-}(CF_3)_2Pz]Cu(H_2C=CHC_2H_5)\}_2$ ($[Cu—Br.(C_4H_8)]_2$) from 1-butene and $\{[3,5\text{-}(CF_3)_2Pz]Cu\}_3$ ($[Cu—H]_3$) and $\{[4\text{-Br-3,5-}(CF_3)_2Pz]Cu\}_3$ ($[Cu—Br]_3$) precursors. Products with both trans- and cis-oriented 1-butene groups are illustrated.

Br.(C$_4$H$_8$)]$_2$, respectively (FIG. 7). The alkene products are obtained as colorless crystalline solids upon cooling the solutions under a 1-butene atmosphere. These [Cu—H.(C$_4$H$_8$)]$_2$ and [Cu—Br.(C$_4$H$_8$)]$_2$ complexes quickly lose 1-butene under reduced pressure, and more slowly upon exposure to air, reverting to the precursor pyrazolates [Cu—H]$_3$ and [Cu—Br]$_3$ as evident from the spectroscopic and elemental analysis data of vacuum dried materials. The 1-butene loss is somewhat faster in [Cu—H.(C$_4$H$_8$)]$_2$.

The [Cu—H.(C$_4$H$_8$)]$_2$ and [Cu—Br.(C$_4$H$_8$)]$_2$ complexes were isolated for spectroscopic studies without significant loss of 1-butene by drying crystalline samples using a gentle stream of 1-butene. Raman data of the solid samples indicate the presence of signals attributable to copper bound 1-butene (C=C stretching bands at 1534 and 1535 cm$^{-1}$) for [Cu—H.(C$_4$H$_8$)]$_2$ and [Cu—Br.(C$_4$H$_8$)]$_2$, respectively. These values represent a significant reduction (~108 cm$^{-1}$) in C=C stretch energy relative to that of the free 1-butene (1643 cm$^{-1}$), as expected from the σ- and π-interactions of olefin with the copper(I). Related propene and ethene complexes of copper, [Cu—H.(C$_3$H$_6$)]$_2$ and [Cu—H.(C$_2$H$_4$)]$_2$ show 110 and 86 cm$^{-1}$ reduction in C=C stretching frequency upon coordination, relative to the corresponding free olefins.

Figure 8:
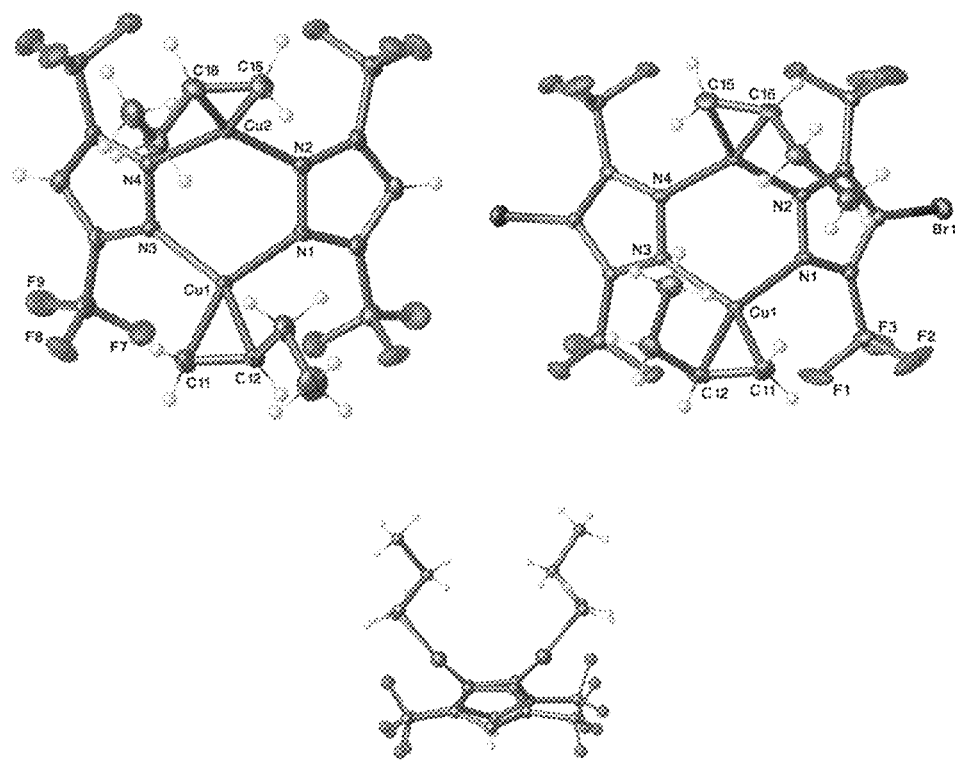
FIG. 8 contains molecular structures of $\{[3,5\text{-}(CF_3)_2Pz]Cu(H_2C=CHC_2H_5)\}_2$ ($[Cu—H.(C_4H_8)]_2$, left) and $\{[4\text{-Br-}3,5\text{-}(CF_3)_2Pz]Cu(H_2C=CHC_2H_5)\}_2$ ($[Cu—Br.(C_4H_8)]_2$, right), and view of the boat-shaped $Cu_2N_4$ core in $[Cu—H.(C_4H_8)]_2$.

Crystals of [Cu—H.(C$_4$H$_8$)]$_2$ and [Cu—Br.(C$_4$H$_8$)]$_2$ were investigated using X-ray crystallography at 100 K (FIG. 8). In contrast to the trinuclear and planar precursors [Cu—H]$_3$ and [Cu—Br]$_3$, 1-butene complexes are dinuclear species with six-membered Cu$_2$N$_4$ cores that adopt boat conformations. The copper centers have a trigonal planar geometry. The two η$^2$-bound, 1-butene moieties display trans-orientation (FIG. 8), although both trans- and cis-orientation of the olefinic moieties are observed in the related propene complex in the solid state, which may be due to accommodating the sterics of the larger 1-butene moieties.

Selected bond distances and angles of [Cu—H.(C$_4$H$_8$)]$_2$ and [Cu—Br.(C$_4$H$_8$)]$_2$, as well as of the analogous propene and ethene complexes are summarized in Table 1. There are no structurally characterized 1-butene complexes of copper for comparison.

olefinic plane (as evident from the Cu—C=C-Et torsion angle) also provides clues to the magnitude of σ/π-bonding interaction between Cu(I) and olefin of [Cu—H.(C$_4$H$_8$)]$_2$ and [Cu—Br.(C$_4$H$_8$)]$_2$, and they are ay. 101.9° and 102.7° for the two complexes. They show much smaller bending of the ethyl substituent out of the olefinic plane, relatively to 1-butene complexes of Zr(II), Ta(III), and Pt(II) (their M-C=C-Et torsion angles are 125.2°, 121.7°, and 109.6°, respectively), and follow the observations noted for a larger data pool involving styrene and metal ions.

A comparison of metrical parameters of [Cu—H.(C$_4$H$_8$)]$_2$ and [Cu—Br.(C$_4$H$_8$)]$_2$ to their ethene and propene counterparts (Table 1) show that the C=C bond lengths and Cu—C distances are very similar for these copper olefin complexes. For example, average C=C distances vary from 1.364-1.374 Å, suggesting that the alkyl chain folds away and the sterics do not affect alkene coordination in these systems. All these copper(I)-olefin complexes feature boat-shaped Cu$_2$N$_4$ cores, but even planar conformation was observed in a copper(I) carbonyl complex [Cu—H.(CO)]$_2$ (which however involves, different, head-on bound CO than side-on bound olefin ligands).

[Cu—H.(C$_4$H$_8$)]$_2$ and [Cu—Br.(C$_4$H$_8$)]$_2$ was investigated as well as the corresponding propene and ethene complexes computationally using dispersion corrected DFT including both trans- and cis-isomers of 1-butene and propene complexes in terms of olefin orientation. Available experimental data agree with the metrical parameters of the optimized structures. For 1-butene complexes, the trans-species is favoured by 0.93 and 1.41 kcal·mol$^{-1}$ (3.9 and 5.9 kJ·mol$^{-1}$) for [Cu—H.(C$_4$H$_8$)]$_2$ and [Cu—Br.(C$_4$H$_8$)]$_2$, respectively. For the propene species [Cu—H.(C$_3$H$_6$)]$_2$ in which both cis- and trans-conformations were observed in crystalline products, the two isomers are energetically degenerate, while for [Cu—Br.(C$_3$H$_6$)]$_2$, the cis-isomer is favoured by a small margin, 0.32 kcal·mol$^{-1}$.

The calculated Raman ν(CH$_2$=CH$_2$), ν(H$_2$C=CHCH$_3$), and ν(H$_2$C=CHC$_2$H$_5$) for the most favoured isomer exhibit values of 1524, 1525, 1517 cm$^{-1}$ respectively, for the [Cu—H] systems, and 1533, 1535 and 1519 cm$^{-1}$ for the [Cu—Br] counterparts. Such values are in line with the experimental

TABLE 1

Selected bond distances (Å) and angles (deg) of copper(I) 1-butene complexes, [Cu—H•(C$_4$H$_8$)]$_2$ and [Cu—Br•(C$_4$H$_8$)]$_2$

| Compound | C=C | Cu—C(H$_2$) | Cu—C(H)Et | C—Cu—C | Cu—C—C—Et |
|---|---|---|---|---|---|
| [Cu—H•(C$_4$H$_8$)]$_2$ | 1.382(12) | 2.004(8) | 2.036(8) | 40.0(3) | 101.4 |
| trans-orientation | 1.364(12) | 2.014(8) | 2.016(8) | 39.6(3) | 100.7 |
| (two molecules in the | 1.373(13) | 2.010(8) | 2.040(7) | 39.6(4) | 102.3 |
| asymmetric unit) | 1.371(12) | 2.018(8) | 2.036(8) | 39.5(3) | 103.0 |
|  | Av. 1.373 | Av. 2.011 | Av. 2.032 | Av. 39.4 |  |
| [Cu—Br•(C$_4$H$_8$)]$_2$ | 1.368(5) | 2.031(3) | 2.047(3) | 39.21(14) | 100.6 |
| trans-orientation | 1.369(5) | 2.019(3) | 2.061(3) | 39.19(14) | 104.8 |
|  | Av. 1.368 | Av. 2.025 | Av. 2.054 | Av. 39.2 |  |

The average C=C distances of [Cu—H.(C$_4$H$_8$)]$_2$ and [Cu—Br.(C$_4$H$_8$)]$_2$ (1.373 and 1.368 Å, respectively) are slightly longer compared to 1.338 Å in free 1-butene. For comparison, the corresponding distance in the 1-butene complex of (η$^5$-Cp)$_2$Zr(PMe$_3$)(C$_4$H$_8$) is relatively longer at 1.47(1) and 1.42(1) Å (for two independent molecules in the asymmetric unit), while those of (t-Bu$_3$SiO)$_3$Ta(C$_4$H$_8$) and [Ph(Me)CHNH$_2$]PtCl$_2$(C$_4$H$_8$) at 1.395(7), and 1.350(3) Å, respectively are not statistically different considering the esd values. These bond distance values point to a relatively stronger metal-butene bonding interaction in the Zr(II) complex, compared to [Cu—H.(C$_4$H$_8$)]$_2$ and [Cu—Br.(C$_4$H$_8$)]$_2$. The degree of bending of the ethyl substituent out of the data, denoting a slight weakening of the Cu-alkene interaction for the brominated species. For comparison, computed ν(C=C) for free ethene, propene, and 1-butene are 1634, 1649, and 1642 cm$^{-1}$, respectively. Note that in ethylene complexes, it is important to consider ν(C=C) in conjunction with other pieces of evidence such as metric, theoretical, NMR spectroscopic for the analysis of metal-ethene bonding as done in this manuscript because the ν(C=C) stretch may couple with δ(CH$_2$) modes.

To probe the trimer to dimer equilibrium in more detail, $^1$H, $^{13}$C, and $^{19}$F NMR were performed in CDCl$_3$ solution. The dimeric copper 1-butene complexes [Cu—H.(C$_4$H$_8$)]$_2$ and [Cu—Br.(C$_4$H$_8$)]$_2$ exist in equilibrium with the trimeric

[Cu—H]$_3$ and [Cu—Br]$_3$ precursors. For example, the room temperature $^1$H NMR spectrum of [Cu—H.(C$_4$H$_8$)]$_2$ in CDCl$_3$ exhibited two peaks at δ 6.81 and δ 7.02 ppm that can be assigned to the protons on the pyrazolyl rings of [Cu—H.(C$_4$H$_8$)]$_2$ and the precursor [Cu—H]$_3$, respectively. Likewise, signals attributable to bound and free olefins are present but are broad, suggesting the existence of a dynamic equilibrium. $^{19}$F NMR spectrum shows two singlets, one at δ-60.12 and the other at δ-61.04 ppm for the two adducts (peak integration values of $^1$H and $^{19}$F signals point to ~1:1 molar ratio of the two species at 20° C.). Addition of excess 1-butene to this mixture leads to the formation of more [Cu—H.(C$_4$H$_8$)]$_2$ from [Cu—H]$_3$ as evident from the enhancement and diminution of NMR signals corresponding to the former and latter, respectively. Cooling the solution [Cu—H.(C$_4$H$_8$)]$_2$ biases the equilibrium toward [Cu—H.(C$_4$H$_8$)]$_2$, suggesting that the enthalpy change for the binding of 1-butene is exothermic in solution. Van' t Hoff analysis of the VT-NMR data provided the enthalpy change for alkene uptake in solution as −34 kJ per mole of Cu-butene interaction for the formation of [Cu—H.(C$_4$H$_8$)]$_2$. The computed values for this process are in good agreement with the experimental observations (~33.5 and −34.5 kJ·mol$^{-1}$ Cu for the cis- and trans-isomer formation, respectively), giving further credence to the computational results and insights generated (Table 2).

These $^{13}$C NMR chemical shift values represent a coordination induced upfield shift (Δδ=δ(free)−δ(coordinated)) of the CH$_2$= and =CH(Et) resonance by about 33.5 and 34.2 ppm respectively, relative to the corresponding peaks of the free 1-butene (δ 113.2 and 140.7 ppm for methylene and methyne carbon atoms, respectively). Copper complexes of 1-butene are remarkably rare. The $^{13}$C NMR data of [{bis(2-pyridyl)amine}Cu(1-butene)][BF$_4$] are available for comparison, and show that its CH$_2$= and =CH(Et) resonances appear very similar, δ 80.7 and 107.6 ppm, respectively. The 1-butene complex of Fe(II), [(η$^5$-Cp)(CO)$_2$Fe(C$_4$H$_8$)][PF$_6$] in contrast, displays its CH$_2$= and =CH(Et) carbon resonance at a significantly higher upfield region (δ 54.5 and 90.9 ppm, respectively) suggesting a stronger Fe(II)-butene interaction compared to that in [Cu—H.(C$_4$-C$_8$)]$_2$. Both the Raman data and the olefinic carbon upfield shift of [Cu—H.(C$_4$-C$_8$)]$_2$ are in good agreement with the data on other types of olefin-copper complexes (e.g., copper (I) ethene or styrene) in the literatures.

The [Cu—Br.(C$_4$H$_8$)]$_2$ complex shows similar NMR data and enthalpy change value as noted above for the non-brominated, [Cu—H.(C$_4$-C$_8$)]$_2$ (Table 2). Overall, a comparison of $^{13}$C NMR data of butene, propene and ethene complexes of copper(I) systems, [Cu—H] and [Cu—Br], to literature data of d-block olefin complexes suggest that these copper-complexes, provided that there are no other compli-

TABLE 2

Experimental and calculated enthalpy change (—H) given in kJ · mol$^{-1}$, per trimer and per Cu-atom.

| Complexes | ΔH$_{alkene/Cu3}$ (in solution, kJ · mol$^{-1}$) | ΔH$_{alkene/Cu}$ (in solution, kJ · mol$^{-1}$) |
|---|---|---|
| [(3,5-(CF$_3$)$_2$Pz)Cu(H$_2$C=CH$_2$)]$_2$ [Cu—H•(C$_2$H$_4$)]$_2$ | −104 ± 3 (calc. −124.6) | −35 ± 1 |
| [(4-Br-3,5-(CF$_3$)$_2$Pz)Cu(H$_2$C=CH$_2$)]$_2$ [Cu—Br•(C$_2$H$_4$)]$_2$ | −67 ± 5 (calc. −72.8) | −22 ± 2 |
| [(3,5-(CF$_3$)$_2$Pz)Cu(H$_2$C=CHCH$_3$)]$_2$ [Cu—H•(C$_3$H$_6$)]$_2$ | −118 ± 6 (calc. −132.7 cis) (calc. −132.7 trans) | −39 ± 2 |
| [(4-Br-3,5-(CF$_3$)$_2$Pz)Cu(H$_2$C=CHCH$_3$)]$_2$ [Cu—Br•(C$_3$H$_6$)]$_2$ | −101 ± 6 (calc. 109.2 cis) (calc. −108.9 trans) | −34 ± 2 |
| [(3,5-(CF$_3$)$_2$Pz)Cu(H$_2$C=CHC$_2$H$_5$)]$_2$ [Cu—H•(C$_4$H$_8$)]$_2$ | −103 ± 6 (calc. −100.4 cis) (calc. −103.6 trans) | −34 ± 2 |
| [(4-Br-3,5-(CF$_3$)$_2$Pz)Cu(H$_2$C=CHC$_2$H$_5$)]$_2$ [Cu—Br•(C$_4$H$_8$)]$_2$ | −92 ± 5 (calc. −99.1 cis) (calc. −105.0 trans) | −31 ± 2 |

Figure 9:
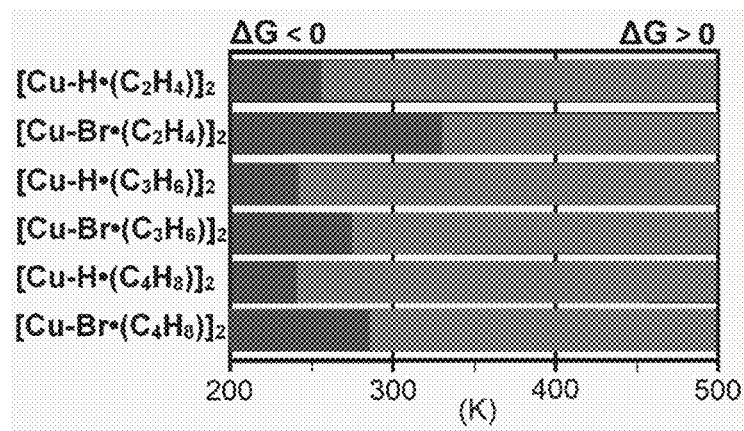
FIG. 9 is a plot of absolute temperature (K) and calculated Gibbs free energy change (kJ·mol$^{-1}$) based on experimental enthalpy and entropy values.

Computed Gibbs free energy (ΔG) based on experimental enthalpy and entropy values (Table 2), indicates that the adduct formation is exothermic below 258 K for [Cu—H.(C$_2$H$_4$)]$_2$, which increases to 327 K for [Cu—Br.(C$_2$H$_4$)]$_2$, in line with the variations observed for respective enthalpy changes (FIG. 9). For [Cu—H.(C$_3$H$_6$)]$_2$ and [Cu—H.(C$_4$H$_8$)]$_2$, ΔG for olefin complex formation is exothermic below 248 K for both adducts, while it increases to 275 K and 288 K, respectively for the corresponding [Cu—Br] derivatives.

Although only trans-[Cu—H.(C$_4$H$_8$)]$_2$ is observed in the solid-state, the $^{19}$F NMR spectrum at −40° C. shows four peaks indicating the existence of both the cis and trans isomers in solution. The $^{13}$C{$^1$H} NMR spectrum also shows two resonances each for the copper bound CH$_2$=(δ 79.4 and 80.0 ppm) and =CH(Et) (δ 106.3 and 106.6 ppm) carbons, consistent with this conclusion. This interesting feature suggests that the steric bulk of the butene approaches a balancing point where both the cis- and trans-isomers are stabilized in solution, but (in contrast to the propene analogues) causes too much steric strain to favour the trans-isomer in the solid-state.

cating factors such as charges, display stronger σ/π-bonding interactions than Ag(I) but weaker than systems involving Au(I), Fe(II) noted above, Ni(0), and Ta(III).

Figure 10:
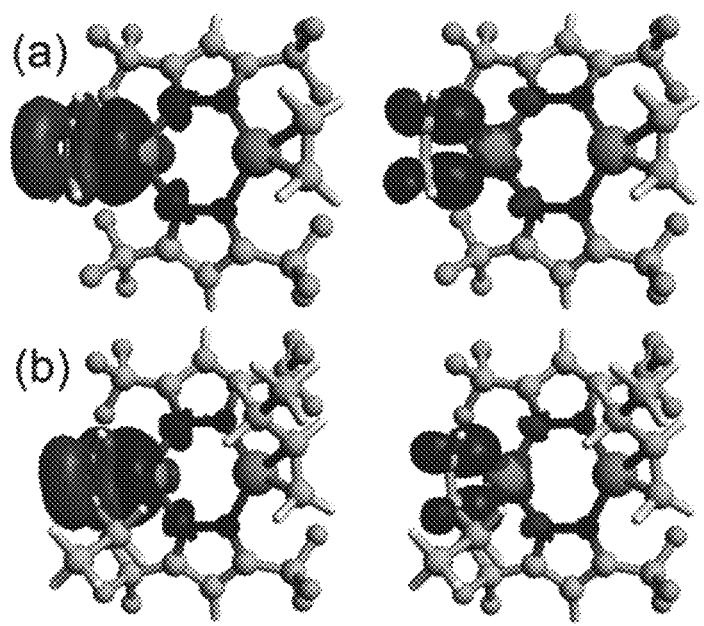
FIG. 10 shows selected deformation densities from the NOCV-EDA analysis, accounting for the σ-donation (left) and π-backbonding (right) in the formation of ethene (a) and 1 butene (b) complexes. Charge flow from red to blue.

To gain a deeper understanding of the nature of copper-olefin interaction in [Cu—H.(olefin)]$_2$, the contributions of different types were evaluated via the Morokuma-Ziegler energy decomposition approach (Table 3), which indicated a value of −42.4 kcal·mol$^{-1}$ for [Cu—H.(C$_2$H$_4$)]$_2$, −44.7 kcal·mol$^{-1}$ for [Cu—H.(C$_3$H$_6$)]$_2$, and −43.6 kcal·mol$^{-1}$ for [Cu—H.(C$_4$-C$_8$)]$_2$. In this framework, the interaction energy (ΔE$_{int}$) shows a more electrostatic character (60%) for [Cu—H.(C$_4$-C$_8$)]$_2$ species, while the orbital character of the interaction accounts for ~33% of the stabilization involving both σ-donation and π-backbonding Cu-olefin bonding patterns (FIG. 10), which contributes similarly to the bonding scheme denoted by ΔE$_{orb}$ stabilizing term (approximately ~41% and ~36%, respectively to ΔE$_{orb}$). Smaller alkenes, ethene and propene also show the same pattern of interaction with copper(I). For related [Cu—Br] species, similar values are obtained for the Cu-olefin interactions. However, changes are observed for Cu-pyrazole interaction, where for [Cu—Br] species, a decrease in energy is given by the smaller electrostatic character of the interaction, in contrast to the orbital and dispersion contribution which remains almost invariant when going from [Cu—H] to [Cu—Br] systems.

Preliminary calculations on isostructural, $[3,5\text{-}(CF_3)_2Pz]^-$ ligand supported Ag(I), Fe(II), and Ni(0) olefin complexes related to the copper adducts investigated in this work exhibit a lowering to $-26.8$ kcal·mol$^{-1}$ of the olefin-metal interaction energy for $[Ag—H.(C_4H_8)]_2$, while the Fe(II) and Ni(0) complexes $\{[Fe—H.(C_4H_8)]_2\}^{2+}$ and $\{[Ni—H.(C_4H_8)]_2\}^{2-}$ show much larger values of $-68.2$ and $-84.3$ kcal·mol$^{-1}$, respectively. These interaction energies point to stronger σ-donor/π-backbonding capabilities of Cu(I) relative to Ag(I), among coinage metals, but not as high as those observed for Fe(II) and Ni(0) in comparable systems.

TABLE 3

Energy decomposition analysis of the interaction energy accounting for the complexation of one alkene group. Values in kcal · mol$^{-1}$. The most favourable isomer was considered.

| | $[Cu—H•(C_2H_4)]_2$ | | $[Cu—H•(C_3H_6)]_2$ | | $[Cu—H•(C_4H_8)]_2$ | |
|---|---|---|---|---|---|---|
| $\Delta E_{Pauli}$ | 113.9 | | 125.9 | | 121.7 | |
| $\Delta E_{elstat}$ | $-92.4$ | 59.2% | $-100.6$ | 59.0% | $-98.6$ | 59.6% |
| $\Delta E_{orb}$ | $-55.8$ | 35.7% | $-58.1$ | 34.0% | $-55.4$ | 33.5% |
| $\Delta E_{disp}$ | $-8.0$ | 5.1% | $-11.8$ | 6.9% | $-11.4$ | 6.9% |
| $\Delta E_{int}$ | $-42.4$ | | $-44.7$ | | $-43.6$ | |
| $\Delta\rho\sigma_{\rightarrow Cu}{}^a$ | $-21.8$ | 39.0% | $-22.0$ | 37.8% | $-22.8$ | 41.1% |
| $\Delta\rho\pi_{\leftarrow Cu}{}^b$ | $-20.3$ | 36.3% | $-19.6$ | 33.8% | $-19.9$ | 36.0% |

$^a$Accounts for the orbital contribution from σ-donation ($\Delta\rho\sigma_{\rightarrow Cu}$) and
$^b$accounts for the orbital contribution from π-backbonding ($\Delta\rho\pi_{\leftarrow Cu}$)

Figure 11:
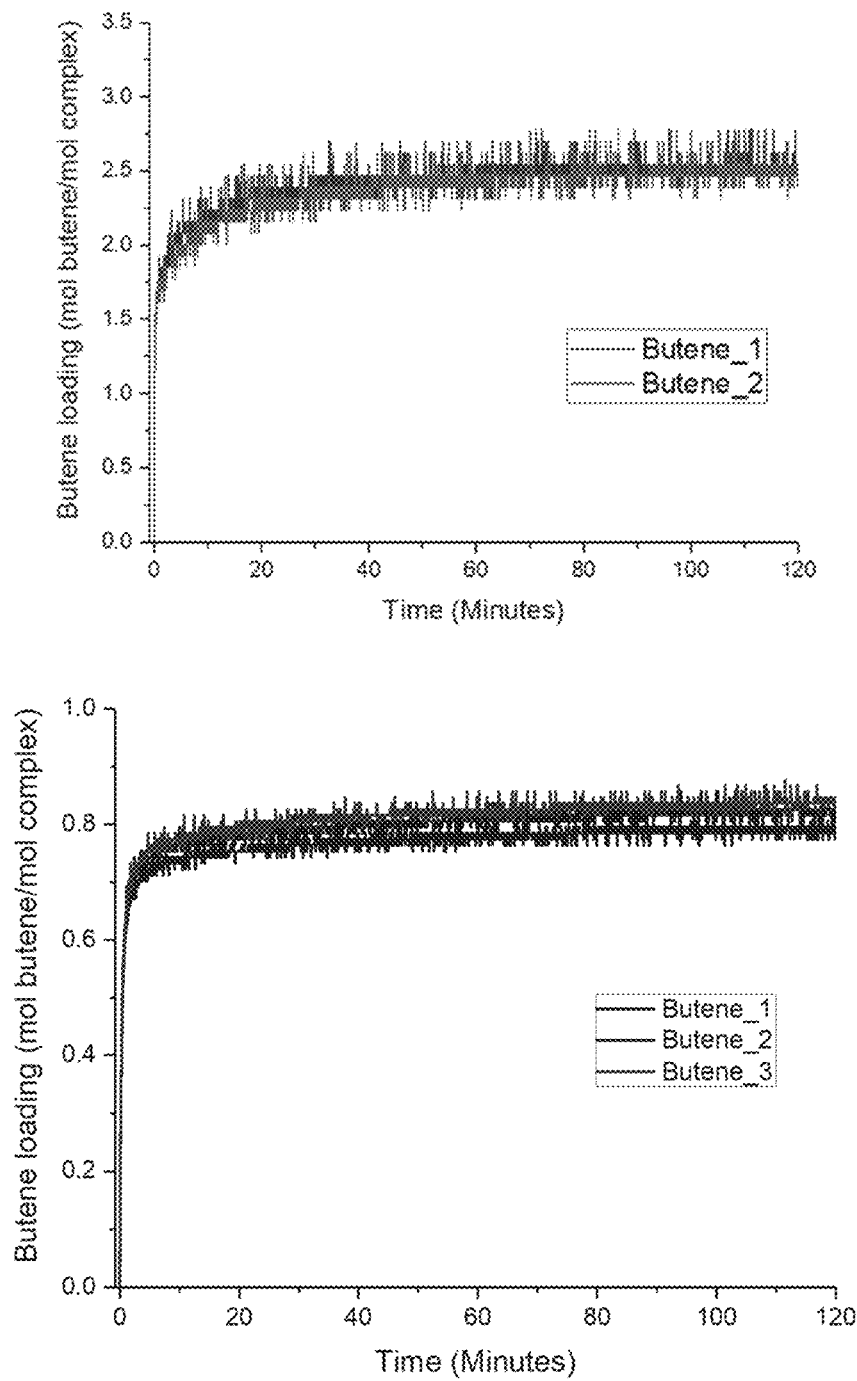
FIG. 11 shows the adsorption of 1-butene into $[Cu—Br]_3$ (top) and $[Cu—H]_3$ (bottom) under a feed pressure of 180 kPa. The "Butene_X" label represents different runs where X is the run number.
Figure 12:
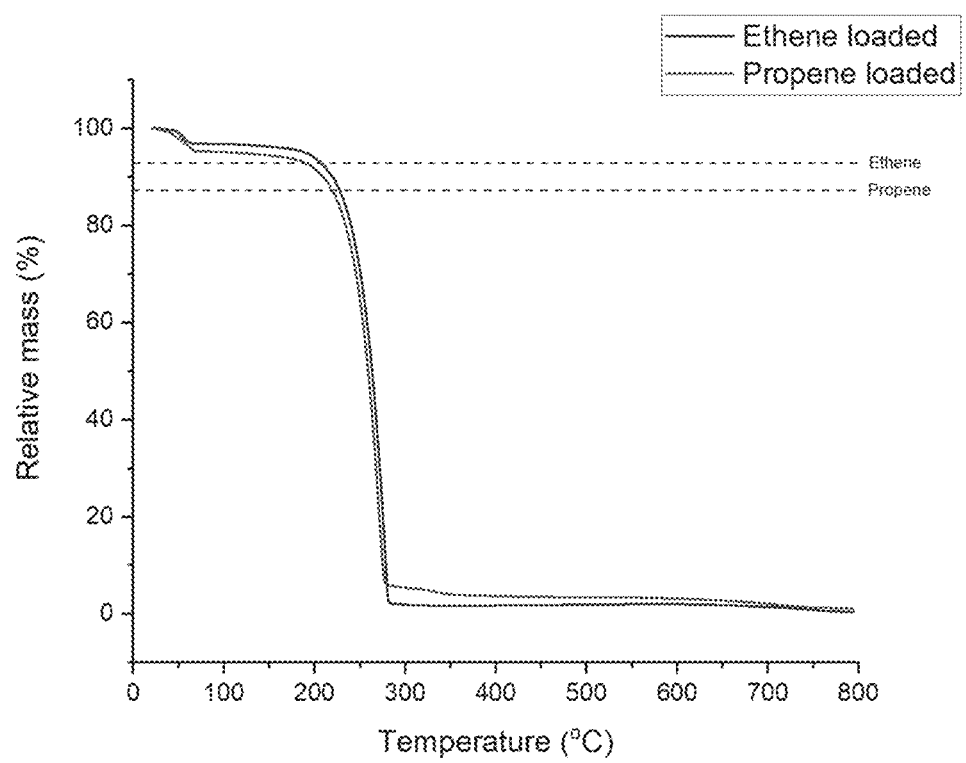
FIGS. 12 and 13 show the mass loss with increasing temperature during TGA analysis on $[Cu—Br]_3$ (FIG. 12) and $[Cu—H]_3$ (FIG. 13) after being loaded with each gas separately (ethene and propene). Both $[Cu—Br]_3$ and $[Cu—H]_3$ rapidly lose bound alkenes when exposed to atmosphere. For $[Cu—Br]_3$ it appears that all gases are desorbed by heating the complex. The complex started to lose ethene at approximately 49° C. and propene at around 43° C. However, calculations showed that only around 40% of the adsorbed amount of each gas was released during the TGA. This indicates that the rest of the adsorbed gas was already released upon exposure to the atmosphere during sample preparation. For $[Cu—H]_3$ it appears that less than 2% of ethene and propene were released during the TGA, which means that they were already desorbed when the adsorbent cell was open to atmosphere. TGA was performed on an Alphatech SDT Q600 TGA/DSC under an inert nitrogen atmosphere. Samples were heated from 20° C. to 800° C. at a rate of 10° C. min$^{-1}$ (Note: dashed lines indicate the expected mass loss.)
Figure 13:
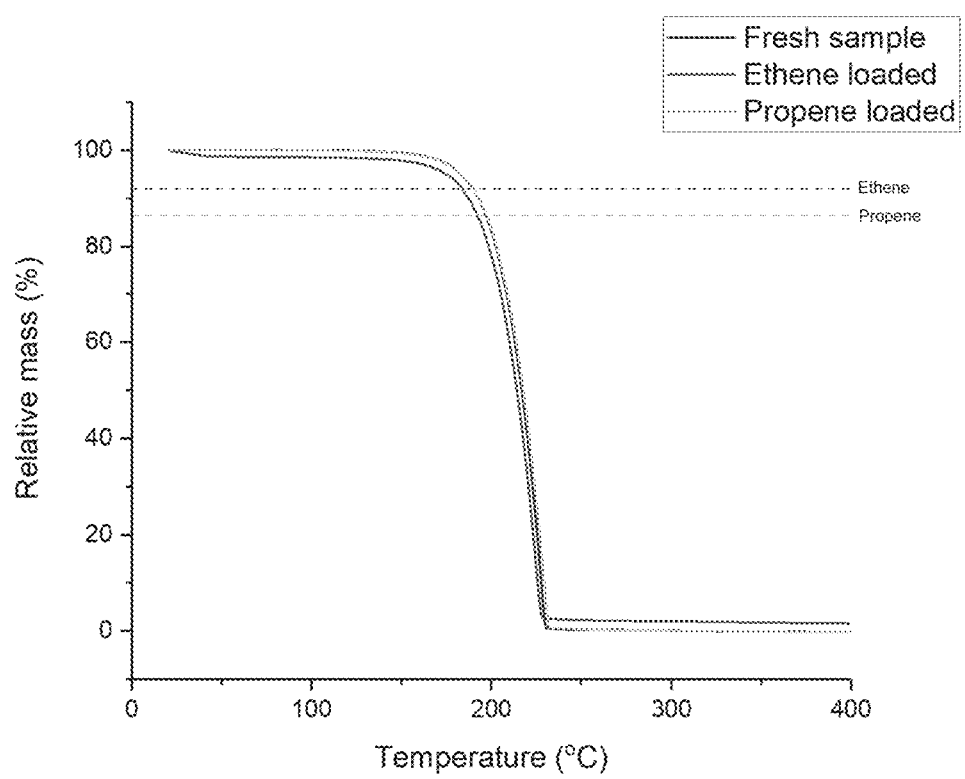

Initial measurements were performed by dosing [Cu—Br]$_3$ and [Cu—H]$_3$ with 1 atm of 1-butene and measuring the pressure drop over a two-hour period (FIG. 11). These experiments showed loadings of 0.15 and 0.27 mol$_{butene}$/mol$_{complex}$, which are comparable to loadings of ethene and propene under similar experimental conditions. Increasing the feed pressure of 1-butene led to loadings of 2.5 and 0.82 mol$_{butene}$/mol$_{complex}$ for [Cu—Br]$_3$ and [Cu—H]$_3$, respectively. This suggests that, despite its larger size, 1-butene is also able to induce the reversible solid-state to solid-state transformation observed for ethene and propene.

The rates of 1-butene, propene, and ethene adsorption into [Cu—Br]$_3$ and [Cu—H]$_3$ are shown in Tables 4 and 5, respectively. Despite the similar or larger kinetic diameter and critical volume of 1-butene (4.46 Å and 240.80 cm$^3$/mol) compared to propene (4.5 Å, 184.6 cm$^3$/mol) and ethene (3.9 Å, 131.1 cm$^3$/mol), 1-butene adsorbed faster into [Cu—Br]$_3$. In contrast, for [Cu—H]$_3$ the rate of 1-butene adsorption was slower than propene and ethene. It is difficult to pin-point this slower 1-butene uptake in [Cu—H]$_3$ to a single clear-cut reason. The gas absorption chemistry in these non-porous [Cu—H]$_3$ and [Cu—Br]$_3$ solids is a complex process, which is accompanied by a separation of trimeric moieties to accommodate 1-butene, large structure-rearrangement involving multiple Cu—N bond breakages and formations, and Cu-olefin bond formations. Furthermore, [Cu—H]$_3$ exists as supramolecular-columns with long inter-trimer Cu . . . Cu interactions while [Cu—Br]$_3$ has a ladder structure with inter-trimer Cu . . . Br contacts.[28, 41]

TABLE 4

The 1-butene, propene, and ethene uptake rates of [Cu—Br]$_3$ measured using the pressure drop method. The adsorption rate is divided into three regions, 0-1 min; 1-40 min; 40-120 min

| Gas | Average rate (0-1 min), (mol$_{ethene}$/mol$_{complex}$/min) | Average rate (1-40 min), (mol$_{ethene}$/mol$_{complex}$/min) | Average rate (40-120 min), (mol$_{ethene}$/mol$_{complex}$/min) |
|---|---|---|---|
| 100 kPa | | | |
| 1-Butene | 0.082 ± 0.004 | 0.0074 ± 0.0001 | 0.0011 ± 0.00003 |
| Propene | 0.023 ± 0.002 | 0.0087 ± 0.001 | 0.0017 ± 0.0006 |
| Ethene | 0.021 ± 0.001 | 0.0075 ± 0.001 | 0.0019 ± 0.0005 |

TABLE 4-continued

The 1-butene, propene, and ethene uptake rates of [Cu—Br]$_3$ measured using the pressure drop method. The adsorption rate is divided into three regions, 0-1 min; 1-40 min; 40-120 min

| Gas | Average rate (0-1 min), (mol$_{ethene}$/mol$_{complex}$/min) | Average rate (1-40 min), (mol$_{ethene}$/mol$_{complex}$/min) | Average rate (40-120 min), (mol$_{ethene}$/mol$_{complex}$/min) |
|---|---|---|---|
| 180 kPa | | | |
| 1-Butene | 1.5 ± 0.04 | 0.018 ± 0 | 0.001 ± 0 |
| 520 kPa | | | |
| Propene | 0.82 ± 0.1 | 0.0011 ± 0.002 | 0.0010 ± 0.0005 |
| 600 kPa | | | |
| Ethene | 1.2 ± 0.01 | 0.0079 ± 0.001 | 0.0005 ± 0.0001 |

TABLE 5

The 1-butene, propene, and ethene uptake rates of [Cu—H]$_3$ measured using the pressure drop method. The adsorption rate is divided into three regions, 0-1 min; 1-40 min; 40-120 min

| Gas | Average rate (0-1 min), (mol$_{ethene}$/mol$_{complex}$/min) | Average rate (1-40 min), (mol$_{ethene}$/mol$_{complex}$/min) | Average rate (40-120 min), (mol$_{ethene}$/mol$_{complex}$/min) |
|---|---|---|---|
| 100 kPa | | | |
| 1-Butene | 0.023 ± 0.005 | 0.0089 ± 0.001 | 0.0008 ± 0.0002 |
| Propene | N/A | N/A | N/A |
| Ethene | N/A | N/A | N/A |
| 180 kPa | | | |
| 1-Butene | 0.59 ± 0.01 | 0.004 ± 0.0003 | 0.0004 ± 0.0002 |
| 520 kPa | | | |
| Propene | 0.82 ± 0.2 | 0.04 ± 0.003 | 0.0015 ± 0.0006 |
| 600 kPa | | | |
| Ethene | 1.2 ± 0.09 | 0.02 ± 0.003 | 0.003 ± 0.0007 |

Quantitative adsorption kinetics are rarely reported in the literature, mainly qualitatively accessed as 'fast' or 'slow' or inferred from breakthrough studies. Data for Zeolite 4A indicated that the porous adsorbent approximated equilibrium capacity within 15 minutes, slightly faster (though not dramatically) than the non-porous adsorbents in this study. This suggests that perceptions of adsorption rate being a fundamental limitation for non-porous adsorbents is based on intuition rather than data.

Retaining operating capacity over multiple cycles is key to adsorbent performance in an industrial process. The non-porous adsorbents [Cu—Br]$_3$ and [Cu—H]$_3$ retained capacity over 5 cycles of ethene, propene, and 1-butene at 1 bar and the higher pressures as indicated in Tables 4 and 5. This extensive cycling (up to 30 cycles without degradation) supports the potential application of these complexes to gas separation processes.

Desorption is another vital parameter to evaluate for potential applications to gas separations processes. Samples of [Cu—H.(C$_4$H$_8$)]$_2$ and [Cu—Br.(C$_4$H$_8$)]$_2$ were qualitatively observed to slowly lose 1-butene when exposed to atmosphere, similar to the ethene and propene complexes reported previously. Because of the relatively slow rate of butene loss, thermogravimetric analysis (TGA) was used to evaluate the thermal desorption conditions required to regenerate the 1-butene complexes of [Cu—Br]$_3$ and [Cu—H]$_3$. The [Cu—Br]$_3$, previously also reported to lose ethene and propene slowly, retained some 1-butene up to ca. 175° C. then began to decompose. In contrast, [Cu—H]$_3$ had already lost ca. half its 1-butene loading by the time it was unloaded from the high-pressure cell (ca. 5 minutes) and completed desorption by ca. 50° C., which may be more related to the time of exposure to atmosphere than heating. [Cu—H]$_3$ and [Cu—Br]$_3$ showed similar decomposition temperatures (175° C.). The relatively large size of 1-butene and its ability to rapidly desorb through dense [Cu—H]$_3$ raises further intriguing questions about the mechanism of adsorption and desorption of gas molecules through these dense crystalline materials.

Positron Annihilation Spectroscopy (PALS) was performed to provide insight into the differences in rate of adsorption and desorption for [Cu—Br]$_3$ and [Cu—H]$_3$ (Table 6). PALS is an emerging characterization technique which uses positrons to probe the free-volume elements within materials. Positrons are attracted to areas of low electron density and will annihilate when interacting with matter, therefore the lifetime (T3) is proportional to the size of the free volume elements (Diameter 3) within the material. The associated Intensity (I$_3$) is related to the relative number of free volume elements. The average free volume element sizes within [Cu—Br]$_3$, and [Cu—H]$_3$ were 0.581, and 0.301 nm respectively. [Cu—Br]$_3$, had the larger average free volume element size, allowing for the high uptakes at ≤100 kPa. The sample, however, caused positron inhibition as was evidenced from the very low intensity <1%. Therefore, I$_3$ is not representative of the number of free volume elements within the sample. Although [Cu—H]₃ had the shorter lifetime, and hence smaller free volume element size, it featured high Intensity, therefore showing considerable number of accessible free volume elements. The smaller free volume element size, 0.3 nm, is too small for the adsorption of ethene or butene through the solid which would explain why increased pressure is needed to convert the structure. The size difference could also account for the faster rate of uptake for [Cu—Br]₃ compared to [Cu—H]₃. The kinetics of desorption were too fast to observe the structural changes from ethene treatment and needs high pressure analysis.

TABLE 6

PALS results for solid [Cu—Br]₃ and [Cu—H]₃ under dynamic vacuum.

| | | Lifetimes | | Intensity | | Free Volume Element Sizes Diameter | |
|---|---|---|---|---|---|---|---|
| Sample | Treatment | $\tau_3$ (ns) | ± | $I_3$ (%) | ± | 3 (nm) | ± |
| [Cu—Br]₃ | Vacuum | 2.057 | 0.195 | 0.6 | 0.1 | 0.581 | 0.035 |
| [Cu—H]₃ | Vacuum | 0.911 | 0.005 | 34.1 | 1.3 | 0.301 | 0.002 |

1-Butene was reacted with [Cu—Br]₃ and [Cu—H]₃ in both the solution and solid states. In solution, the trimeric species rearrange to the dimeric complexes [Cu—Br.(C₄H₈)]₂ and ([Cu—H.(C₄H₈)]₂. NMR, Raman, X-ray, and computational studies were used to examine the nature of the copper(I)-alkene interactions and compare the bonding, structural and spectroscopic features in the ethene, propene, butene series. For the first time, copper(I) complexes of 1-butene were characterized using single crystal X-ray crystallography. Isolable [Cu—H.(C₄H₈)]₂ and [Cu—Br.(C₄H₈)]₂ would serve as useful models for species that may be present in copper containing porous materials or solutions[18, 20] utilized for 1-butene/butane separation. The adsorption of gaseous 1-butene by solid [Cu—Br]₃ and [Cu—H]₃ also has remarkable features. The significantly larger 1-butene is somehow able to penetrate the dense solid material and to coordinate with copper(I) ions at high molar occupancy. The adsorption of 1-butene into these nonporous adsorbents occurs over similar timescales to porous adsorbents, removing one roadblock towards application in gas separations.

What is claimed is:

1. A composition comprising an alkene and a compound having Formula I:

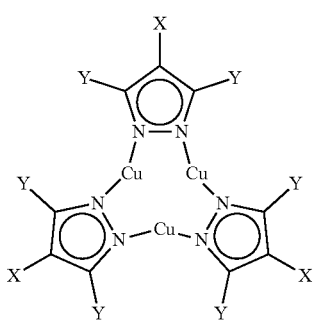

wherein each X is, independent of the other, chosen from H and Br; and each Y is, independent of the other, chose from CF₃, C₂F₅, C₃F₇, C₄F₈, F, Cl, Br, and I.

2. The composition of claim 1, wherein the alkene is ethene, propene, 1-butene, or a mixture thereof.

3. The composition of claim 1, wherein Y is CF₃.

4. The composition of claim 1, further comprising an alkane.

5. The composition of claim 1, further comprising a complex having Formula II:

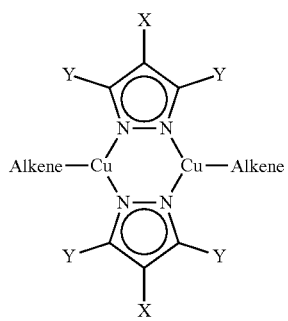

wherein each X is, independent of the other, chosen from H and Br; and each Y is, independent of the other, chosen from CF₃, C₂F₅, C₃F₇, C₄F₈, F, Cl, Br, and I.

6. The composition of claim 5, wherein Alkene is ethene, propene, or 1-butene.

7. A complex having Formula II:

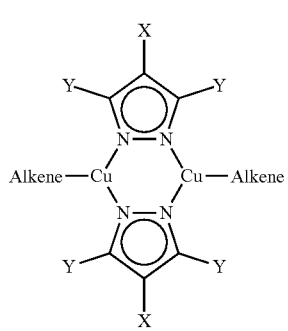

wherein each X is, independent of the other, chosen from H and Br; and each Y is, independent of the other, chosen from CF₃, C₂F₅, C₃F₇, C₄F₈, F, Cl, Br, and I.

8. The complex of claim 7, wherein Alkene is ethene, propene, or 1-butene.

9. The complex of claim 7, wherein Y is CF₃.

10. A method of separating an alkene from a mixture comprising the alkene and an alkane, comprising: contacting the mixture with a compound having Formula I:

I

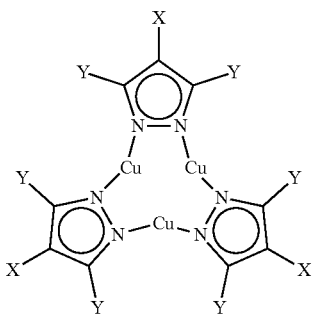

to form a complex having Formula II

II

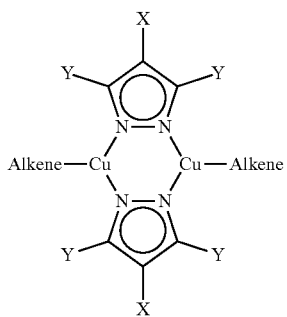

wherein each X is, independent of the other, chosen from H and Br; and each Y is, independent of the other, chosen from $CF_3$, $C_2F_5$, $C_3F_7$, $C_4F_8$, F, Cl, Br, and I.

11. The method of claim 10, wherein Y is $CF_3$.

12. The method of claim 10, wherein the alkene is ethene, propene, 1-butene, or a mixture thereof.

13. The method of claim 10, wherein the alkane is ethane, propane, butane, or a mixture thereof.

14. The method of claim 10, wherein the mixture is contacted with the compound having Formula I at a pressure below a partial pressure of the alkene.

15. The method of claim 10, wherein the mixture is contacted with the compound having Formula I at a temperature from 0° C. to 200° C.

16. The method of claim 10, wherein the mixture is contacted with the compound having Formula I at a pressure from ambient pressure to 100 kPa.

17. The method of claim 10, wherein the mixture is contacted with the compound having Formula I at a pressure from 100 kPa to 100,000 kPa.

18. The method of claim 10, wherein the mixture is contacted with the compound having Formula I at a pressure from 600 kPa to 1000 kPa.

19. The method of claim 10, further comprising reducing pressure to ambient pressure or below after forming the complex having Formula II, and collecting the alkene.

20. The method of claim 10, further comprising increasing temperature after forming the complex having Formula II, and collecting the alkene.

21. The method of claim 10, wherein the mixture is contacted with the compound having Formula I in the presence of a solvent.

\* \* \* \* \*